United States Patent
Hötten et al.

(10) Patent No.: US 7,025,959 B1
(45) Date of Patent: Apr. 11, 2006

(54) MP121, A GROWTH/DIFFERENTIATION FACTOR OF THE TGF-β FAMILY

(75) Inventors: Gertrud Hötten, Herne (DE); Helge Neidhardt, Marburg (DE); Rolf Bechtold, Heidelberg (DE); Jens Pohl, Hambrücken (DE); Michael Paulista, Leimen (DE)

(73) Assignee: Biopharm Gesellschaft Zur Biotechnologischen Entwicklung von Pharmaka mbH, Heidelberg (DE)

( * ) Notice: Subject to any disclaimer, the term of this patent is extended or adjusted under 35 U.S.C. 154(b) by 210 days.

(21) Appl. No.: 09/684,383

(22) Filed: Oct. 10, 2000

Related U.S. Application Data

(60) Division of application No. 09/218,176, filed on Dec. 22, 1998, now Pat. No. 6,171,584, which is a continuation of application No. 08/679,048, filed on Jul. 12, 1996, now abandoned, which is a continuation-in-part of application No. 08/482,577, filed on Jun. 7, 1995, now Pat. No. 5,807,713, which is a continuation-in-part of application No. 08/289,222, filed on Aug. 12, 1994, now Pat. No. 6,120,760, which is a continuation-in-part of application No. PCT/EP93/00350, filed on Feb. 12, 1993.

(30) Foreign Application Priority Data

| | | |
|---|---|---|
| Feb. 12, 1992 | (EP) | ................................ 92102324 |
| Jul. 1, 1994 | (DE) | ................................ 44 23 190 |
| Mar. 27, 1995 | (DE) | ................................ 195 11 243 |
| Jul. 12, 1996 | (WO) | ................... PCT/EP96/03065 |

(51) Int. Cl.
 *C12N 15/19* (2006.01)
 *C07K 14/52* (2006.01)
 *A61K 38/19* (2006.01)

(52) U.S. Cl. ................. 424/85.1; 530/351; 530/402; 514/2; 514/8; 514/12; 536/23.5; 536/24.3

(58) Field of Classification Search ................ 530/350, 530/351, 402; 514/2, 8, 12; 424/85.1
See application file for complete search history.

(56) References Cited

U.S. PATENT DOCUMENTS

| | | | |
|---|---|---|---|
| 4,798,885 A | 1/1989 | Mason et al. | ............... 530/350 |
| 6,120,760 A * | 9/2000 | Hotten et al. | .............. 424/85.1 |

FOREIGN PATENT DOCUMENTS

| | | |
|---|---|---|
| EP | 0 222 491 | 5/1987 |
| WO | 93/16099 | 8/1993 |
| WO | 95/04819 | 2/1995 |
| WO | PCT/EP95/02552 | 6/1995 |
| WO | 96/01316 | 1/1996 |

OTHER PUBLICATIONS

Ganong et al. Review of Medical Physiology 17th edition Appleton & Lange, pp. 220, 446, 1995.*
Recek et al. Cell, vol. 50, p. 667, 1987.*
Creighton, Proteins, Freeman & Co. pp. 70-73, Structures & Principles, 1984.*
Callard & Gearing (1994) The Cytokine Factsbook. Academic Press Ltd. p. 39.*
Hötten et al., "Cloning of a New Member of the TGF-β Family: A putative New Activin β_c Chain", Biochem. & Biophys. Res. Comm., vol. 206, No. 2, 1995.
Forage et al (1986) Proc. Natl. Acad. Sci. vol. 83, pp. 3091-3095.
Bowie et al (1990) Science vol. 247, pp. 1306-1310.

* cited by examiner

*Primary Examiner*—Prema Mertz
(74) *Attorney, Agent, or Firm*—Rothwell Figg Ernst & Manbeck

(57) ABSTRACT

The invention concerns a protein of the TGF-β family, the DNA coding therefor and a pharmaceutical composition containing such protein.

20 Claims, 8 Drawing Sheets

Fig. 1

```
              10          20          30          40
MP121     CCRQEFFVDF  REIGWHDWII  QPEGYAMNFC  IGQCPLHIAG
INHIB βA  CCKKQFFVSF  KDIGWNDWII  APSGYHANYC  EGECPSHIAG
INHIB βB  CCRQQFFIDF  RLIGWNDWII  APTGYYGNYC  EGSCPAYLAG
INHIB α   CHRVALNISF  QELGWERWIV  YPPSFIFHYC  HGGCGLHIP-
          *+++ ++++*  +++** +**+  * ++  + *   * *+++++++

50          60          70          80
MP121     MPGIAASFHT  AVLNLLKANT  AAGTTGGGSC  C--VPTARRP
INHIB βA  TSGSSLSFHS  TVINHYRMRG  HSPFANLKSC  C--VPTKLRP
INHIB βB  VPGSASSFHT  AVVNQYRMRG  LNP-GTVNSC  C--IPTKLST
INHIB α   ---PNLSLPV  PGAPPTPAQP  YSLLPGAQPC  CAALPGTMRP
          ++ + *+++  ++ +   +     + +* *  +*+  ++

90         100         110
MP121     LSLLYYDRDS  NIVKTD-IPD  MVVEACGCS
INHIB βA  MSMLYYDDGQ  NIIKKD-IQN  MIVEECGCS
INHIB βB  MSMLYFDDEY  NIVKRD-VPN  MIVEECGCA
INHIB α   LHVRTTSDGG  YSFKYETVPN  LLTQHCACI
          ++ ++++     +++* + ++    + ++ *+*+
```

Fig. 2a    [EcoRI] [NcoI]

| | |
|---|---|
| OD | ATGAATTCCCATGGACCTGGGCTGGHAKGAHTGGAT |
| BMP 2 | ACGTGGGGTGGAATGACTGGAT |
| BMP 3 | ATATTGGCTGGAGTGAATGGAT |
| BMP 4 | ATGTGGGCTGGAATGACTGGAT |
| BMP 7 | ACCTGGGCTGGCAGGACTGGAT |
| TGF-β1 | AGGACCTCGGCTGGAAGTGGAT |
| TGF-β2 | GGGATCTAGGGTGGAAATGGAT |
| TGF-β3 | AGGATCTGGGCTGGA'GTGGGT |
| INHIBIN α | AGCTGGGCTGGGAACGGTGGAT |
| INHIBIN β$_A$ | ACATCGGCTGGAATGACTGGAT |
| INHIBIN β$_B$ | TCATCGGCTGGAACGACTGGAT |

Fig. 2b    EcoRI

| | |
|---|---|
| OID | ATGAATTCGAGCTGCGTSGGSRCACAGCA |
| BMP 2 | GAGTTCTGTCGGGACACAGCA |
| BMP 3 | CATCTTTTCTGGTACACAGCA |
| BMP 4 | CAGTTCAGTGGGCACACAACA |
| BMP 7 | GAGCTGCGTGGGCGCACAGCA |
| TGF-β1 | CAGCGCCTGCGGCACGCAGCA |
| TGF-β2 | TAAATCTTGGGACACGCAGCA |
| TGF-β3 | CAGGTCCTGGGGCACGCAGCA |
| INHIBIN α | CCCTGGGAGAGCAGCACAGCA |
| INHIBIN β$_A$ | CAGCTTGGTGGGCACACAGCA |
| INHIBIN β$_B$ | CAGCTTGGTGGGAATGCAGCA |

PRECURSOR

MATURE DIMER

MATURE MONOMER

REDUCED PRECURSOR

REDUCED MATURE MONOMER

SEQUENCE LISTING (1) GENERAL INFORMATION:

(iii) NUMBER OF SEQUENCES: 31

(2) INFORMATION FOR SEQ ID NO: 1:

(i) SEQUENCE CHARACTERISTICS:
      (A) LENGTH: 176 amino acids
      (B) TYPE: amino acid
      (C) STRANDEDNESS: single
      (D) TOPOLOGY: linear (ii) MOLECULE TYPE: protein (xi) SEQUENCE DESCRIPTION: SEQ ID NO: 1:

```
Cys Gly Pro Gly Arg Gly Pro Val Gly Arg Arg Arg Tyr Ala Arg Lys
 1               5                  10                  15

Gln Leu Val Pro Leu Leu Tyr Lys Gln Phe Val Pro Gly Val Pro Glu
             20                  25                  30

Arg Thr Leu Gly Ala Ser Gly Pro Ala Glu Gly Arg Val Ala Arg Gly
         35                  40                  45

Ser Glu Arg Phe Arg Asp Leu Val Pro Asn Tyr Asn Pro Asp Ile Ile
     50                  55                  60

Phe Lys Asp Glu Glu Asn Ser Gly Ala Asp Arg Leu Met Thr Glu Arg
 65                  70                  75                  80
```

```
Cys Lys Glu Arg Val Asn Ala Leu Ala Ile Ala Val Met Asn Met Trp
                85                  90                  95

Pro Gly Val Arg Leu Arg Val Thr Glu Gly Trp Asp Glu Asp Gly His
            100                 105                 110

His Ala Gln Asp Ser Leu His Tyr Glu Gly Arg Ala Leu Asp Ile Thr
        115                 120                 125

Thr Ser Asp Arg Asp Arg Asn Lys Tyr Gly Leu Leu Ala Arg Leu Ala
    130                 135                 140

Val Glu Ala Gly Phe Asp Trp Val Tyr Tyr Glu Ser Arg Asn His Ile
145                 150                 155                 160

His Val Ser Val Lys Ala Asp Asn Ser Leu Ala Val Arg Ala Gly Gly
                165                 170                 175
```

(2) INFORMATION FOR SEQ ID NO: 2:

(i) SEQUENCE CHARACTERISTICS:
        (A) LENGTH: 374 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: mat peptide
        (B) LOCATION: 1..176
        (C) IDENTIFICATION METHOD: S (xi) SEQUENCE DESCRIPTION: SEQ ID NO: 2:

```
Cys Gly Pro Gly Arg Gly Pro Val Gly Arg Arg Tyr Ala Arg Lys
  1               5                  10                  15

Gln Leu Val Pro Leu Tyr Lys Gln Phe Val Pro Gly Val Pro Glu
                20                  25                  30

Arg Thr Leu Gly Ala Ser Gly Pro Ala Glu Gly Arg Val Ala Arg Gly
            35                  40                  45

Ser Glu Arg Phe Arg Asp Leu Val Pro Asn Tyr Asn Pro Asp Ile Ile
    50                  55                  60

Phe Lys Asp Glu Glu Asn Ser Gly Ala Asp Arg Leu Met Thr Glu Arg
 65                  70                  75                  80

Cys Lys Glu Arg Val Asn Ala Leu Ala Ile Ala Val Met Asn Met Trp
                85                  90                  95

Pro Gly Val Arg Leu Arg Val Thr Glu Gly Trp Asp Glu Asp Gly His
            100                 105                 110

His Ala Gln Asp Ser Leu His Tyr Glu Gly Arg Ala Leu Asp Ile Thr
        115                 120                 125

Thr Ser Asp Arg Asp Arg Asn Lys Tyr Gly Leu Leu Ala Arg Leu Ala
    130                 135                 140

Val Glu Ala Gly Phe Asp Trp Val Tyr Tyr Glu Ser Arg Asn His Ile
145                 150                 155                 160

His Val Ser Val Lys Ala Asp Asn Ser Leu Ala Val Arg Ala Gly Gly
                165                 170                 175

Cys Phe Pro Gly Asn Ala Thr Val Arg Leu Trp Ser Gly Glu Arg Lys
            180                 185                 190

Gly Leu Arg Glu Leu His Arg Gly Asp Trp Val Leu Thr Ala Asp Ala
        195                 200                 205

Ser Gly Arg Val Val Pro Thr Pro Val Leu Leu Phe Leu Asp Arg Asp
    210                 215                 220

Leu Gln Arg Arg Ala Ser Phe Val Ala Val Glu Thr Glu Trp Pro Pro
```

```
                225                 230                 235                 240
Arg Lys Leu Leu Leu Thr Pro Trp His Leu Val Phe Ala Ala Arg Gly
                    245                 250                 255

Pro Ala Pro Ala Pro Gly Asp Phe Ala Pro Val Phe Ala Arg Arg Leu
                    260                 265                 270

Arg Ala Gly Asp Ser Val Leu Ala Pro Gly Gly Asp Ala Leu Arg Pro
                    275                 280                 285

Ala Arg Val Ala Arg Val Ala Arg Glu Glu Ala Val Gly Val Phe Ala
    290                 295                 300

Pro Leu Thr Ala His Gly Thr Leu Leu Val Asn Asp Val Leu Ala Ser
305                 310                 315                 320

Cys Tyr Ala Val Leu Glu Ser His Gln Trp Ala His Arg Ala Phe Ala
                    325                 330                 335

Pro Leu Arg Leu Leu His Ala Leu Gly Ala Leu Leu Pro Gly Gly Ala
                    340                 345                 350

Val Gln Pro Thr Gly Met His Trp Tyr Ser Arg Leu Leu Tyr Arg Leu
                    355                 360                 365

Ala Glu Glu Leu Leu Gly
    370

(2) INFORMATION FOR SEQ ID NO: 3:

(i) SEQUENCE CHARACTERISTICS:
        (A) LENGTH: 396 amino acids
        (B) TYPE: amino acid
        (C) STRANDEDNESS: single
        (D) TOPOLOGY: linear (ii) MOLECULE TYPE: protein (ix) FEATURE:
        (A) NAME/KEY: sig peptide
        (B) LOCATION: -22..-1
        (C) IDENTIFICATION METHOD: S
        (A) NAME/KEY: mat peptide
        (B) LOCATION: 1..176
        (C) IDENTIFICATION METHOD: S (xi) SEQUENCE DESCRIPTION: SEQ ID NO: 3:

Met Ala Leu Leu Thr Asn Leu Leu Pro Leu Cys Cys Leu Ala Leu Leu
        -20                 -15                 -10

Ala Leu Pro Ala Gln Ser Cys Gly Pro Gly Arg Gly Pro Val Gly Arg
    -5                   1                   5                  10

Arg Arg Tyr Ala Arg Lys Gln Leu Val Pro Leu Leu Tyr Lys Gln Phe
                    15                  20                  25

Val Pro Gly Val Pro Glu Arg Thr Leu Gly Ala Ser Gly Pro Ala Glu
                    30                  35                  40

Gly Arg Val Ala Arg Gly Ser Glu Arg Phe Arg Asp Leu Val Pro Asn
    45                  50                  55

Tyr Asn Pro Asp Ile Ile Phe Lys Asp Glu Glu Asn Ser Gly Ala Asp
    60                  65                  70

Arg Leu Met Thr Glu Arg Cys Lys Glu Arg Val Asn Ala Leu Ala Ile
75                  80                  85                  90

Ala Val Met Asn Met Trp Pro Gly Val Arg Leu Arg Val Thr Glu Gly
                    95                  100                 105

Trp Asp Glu Asp Gly His His Ala Gln Asp Ser Leu His Tyr Glu Gly
                    110                 115                 120

Arg Ala Leu Asp Ile Thr Thr Ser Asp Arg Asp Arg Asn Lys Tyr Gly
                    125                 130                 135
```

```
Leu Leu Ala Arg Leu Ala Val Glu Ala Gly Phe Asp Trp Val Tyr Tyr
    140                 145                 150

Glu Ser Arg Asn His Ile His Val Ser Val Lys Ala Asp Asn Ser Leu
155                 160                 165                 170

Ala Val Arg Ala Gly Gly Cys Phe Pro Gly Asn Ala Thr Val Arg Leu
                175                 180                 185

Trp Ser Gly Glu Arg Lys Gly Leu Arg Glu Leu His Arg Gly Asp Trp
            190                 195                 200

Val Leu Thr Ala Asp Ala Ser Gly Arg Val Val Pro Thr Pro Val Leu
        205                 210                 215

Leu Phe Leu Asp Arg Asp Leu Gln Arg Arg Ala Ser Phe Val Ala Val
    220                 225                 230

Glu Thr Glu Trp Pro Pro Arg Lys Leu Leu Leu Thr Pro Trp His Leu
235                 240                 245                 250

Val Phe Ala Ala Arg Gly Pro Ala Pro Ala Pro Gly Asp Phe Ala Pro
                255                 260                 265

Val Phe Ala Arg Arg Leu Arg Ala Gly Asp Ser Val Leu Ala Pro Gly
            270                 275                 280

Gly Asp Ala Leu Arg Pro Ala Arg Val Ala Arg Val Ala Arg Glu Glu
        285                 290                 295

Ala Val Gly Val Phe Ala Pro Leu Thr Ala His Gly Thr Leu Leu Val
    300                 305                 310

Asn Asp Val Leu Ala Ser Cys Tyr Ala Val Leu Glu Ser His Gln Trp
315                 320                 325                 330

Ala His Arg Ala Phe Ala Pro Leu Arg Leu Leu His Ala Leu Gly Ala
                335                 340                 345

Leu Leu Pro Gly Gly Ala Val Gln Pro Thr Gly Met His Trp Tyr Ser
            350                 355                 360

Arg Leu Leu Tyr Arg Leu Ala Glu Glu Leu Leu Gly
        365                 370

(2) INFORMATION FOR SEQ ID NO: 4:

(i) SEQUENCE CHARACTERISTICS:
        (A) LENGTH: 528 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: mat peptide
        (B) LOCATION: 1..528
        (C) IDENTIFICATION METHOD: S (xi) SEQUENCE DESCRIPTION: SEQ ID NO: 4:

TGC GGG CCG GGC CGG GGG CCG GTT GGC CGG CGC CGC TAT GCG CGC AAG        48
Cys Gly Pro Gly Arg Gly Pro Val Gly Arg Arg Arg Tyr Ala Arg Lys
  1               5                  10                  15

CAG CTC GTG CCG CTA CTC TAC AAG CAA TTT GTG CCC GGC GTG CCA GAG        96
Gln Leu Val Pro Leu Leu Tyr Lys Gln Phe Val Pro Gly Val Pro Glu
                 20                  25                  30

CGG ACC CTG GGC GCC AGT GGG CCA GCG GAG GGG AGG GTG GCA AGG GGC       144
Arg Thr Leu Gly Ala Ser Gly Pro Ala Glu Gly Arg Val Ala Arg Gly
         35                  40                  45

TCC GAG CGC TTC CGG GAC CTC GTG CCC AAC TAC AAC CCC GAC ATC ATC       192
Ser Glu Arg Phe Arg Asp Leu Val Pro Asn Tyr Asn Pro Asp Ile Ile
 50                  55                  60
```

-continued

```
TTC AAG GAT GAG GAG AAC AGT GGA GCC GAC CGC CTG ATG ACC GAA CGT       240
Phe Lys Asp Glu Glu Asn Ser Gly Ala Asp Arg Leu Met Thr Glu Arg
 65                  70                  75                  80

TGT AAG GAA CGG GTG AAC GCT TTG GCC ATT GCC GTG ATG AAC ATG TGG       288
Cys Lys Glu Arg Val Asn Ala Leu Ala Ile Ala Val Met Asn Met Trp
                 85                  90                  95

CCC GGA GTG CGC CTA CGA GTG ACT GAG GGC TGG GAC GAG GAC GGC CAC       336
Pro Gly Val Arg Leu Arg Val Thr Glu Gly Trp Asp Glu Asp Gly His
             100                 105                 110

CAC GCT CAG GAT TCA CTC CAC TAC GAA GGC CGT GCT TTG GAC ATC ACT       384
His Ala Gln Asp Ser Leu His Tyr Glu Gly Arg Ala Leu Asp Ile Thr
         115                 120                 125

ACG TCT GAC CGC GAC CGC AAC AAG TAT GGG TTG CTG GCG CGC CTC GCA       432
Thr Ser Asp Arg Asp Arg Asn Lys Tyr Gly Leu Leu Ala Arg Leu Ala
     130                 135                 140

GTG GAA GCC GGC TTC GAC TGG GTC TAC TAC GAG TCC CGC AAC CAC ATC       480
Val Glu Ala Gly Phe Asp Trp Val Tyr Tyr Glu Ser Arg Asn His Ile
145                 150                 155                 160

CAC GTG TCG GTC AAA GCT GAT AAC TCA CTG GCG GTC CGG GCG GGC GGC       528
His Val Ser Val Lys Ala Asp Asn Ser Leu Ala Val Arg Ala Gly Gly
                165                 170                 175

(2) INFORMATION FOR SEQ ID NO: 5:

(i) SEQUENCE CHARACTERISTICS:
        (A) LENGTH: 1122 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: mat peptide
        (B) LOCATION: 1..528
        (C) IDENTIFICATION METHOD: S (xi) SEQUENCE DESCRIPTION: SEQ ID NO: 5:

TGC GGG CCG GGC CGG GGG CCG GTT GGC CGG CGC CGC TAT GCG CGC AAG        48
Cys Gly Pro Gly Arg Gly Pro Val Gly Arg Arg Arg Tyr Ala Arg Lys
  1               5                  10                  15

CAG CTC GTG CCG CTA CTC TAC AAG CAA TTT GTG CCC GGC GTG CCA GAG        96
Gln Leu Val Pro Leu Leu Tyr Lys Gln Phe Val Pro Gly Val Pro Glu
                 20                  25                  30

CGG ACC CTG GGC GCC AGT GGG CCA GCG GAG GGG AGG GTG GCA AGG GGC       144
Arg Thr Leu Gly Ala Ser Gly Pro Ala Glu Gly Arg Val Ala Arg Gly
             35                  40                  45

TCC GAG CGC TTC CGG GAC CTC GTG CCC AAC TAC AAC CCC GAC ATC ATC       192
Ser Glu Arg Phe Arg Asp Leu Val Pro Asn Tyr Asn Pro Asp Ile Ile
         50                  55                  60

TTC AAG GAT GAG GAG AAC AGT GGA GCC GAC CGC CTG ATG ACC GAA CGT       240
Phe Lys Asp Glu Glu Asn Ser Gly Ala Asp Arg Leu Met Thr Glu Arg
 65                  70                  75                  80

TGT AAG GAA CGG GTG AAC GCT TTG GCC ATT GCC GTG ATG AAC ATG TGG       288
Cys Lys Glu Arg Val Asn Ala Leu Ala Ile Ala Val Met Asn Met Trp
                 85                  90                  95

CCC GGA GTG CGC CTA CGA GTG ACT GAG GGC TGG GAC GAG GAC GGC CAC       336
Pro Gly Val Arg Leu Arg Val Thr Glu Gly Trp Asp Glu Asp Gly His
             100                 105                 110

CAC GCT CAG GAT TCA CTC CAC TAC GAA GGC CGT GCT TTG GAC ATC ACT       384
His Ala Gln Asp Ser Leu His Tyr Glu Gly Arg Ala Leu Asp Ile Thr
         115                 120                 125
```

-continued

```
ACG TCT GAC CGC GAC CGC AAC AAG TAT GGG TTG CTG GCG CGC CTC GCA        432
Thr Ser Asp Arg Asp Arg Asn Lys Tyr Gly Leu Leu Ala Arg Leu Ala
    130                 135                 140

GTG GAA GCC GGC TTC GAC TGG GTC TAC TAC GAG TCC CGC AAC CAC ATC        480
Val Glu Ala Gly Phe Asp Trp Val Tyr Tyr Glu Ser Arg Asn His Ile
145                 150                 155                 160

CAC GTG TCG GTC AAA GCT GAT AAC TCA CTG GCG GTC CGG GCG GGC GGC        528
His Val Ser Val Lys Ala Asp Asn Ser Leu Ala Val Arg Ala Gly Gly
                165                 170                 175

TGC TTT CCG GGA AAT GCA ACT GTG CGC CTG TGG AGC GGC GAG CGG AAA        576
Cys Phe Pro Gly Asn Ala Thr Val Arg Leu Trp Ser Gly Glu Arg Lys
            180                 185                 190

GGG CTG CGG GAA CTG CAC CGC GGA GAC TGG GTT TTG ACG GCC GAT GCG        624
Gly Leu Arg Glu Leu His Arg Gly Asp Trp Val Leu Thr Ala Asp Ala
        195                 200                 205

TCA GGC CGG GTG GTG CCC ACG CCG GTG CTG CTC TTC CTG GAC CGG GAC        672
Ser Gly Arg Val Val Pro Thr Pro Val Leu Leu Phe Leu Asp Arg Asp
    210                 215                 220

TTG CAG CGC CGG GCT TCA TTT GTG GCT GTG GAG ACC GAG TGG CCT CCA        720
Leu Gln Arg Arg Ala Ser Phe Val Ala Val Glu Thr Glu Trp Pro Pro
225                 230                 235                 240

CGC AAA CTG TTG CTC ACG CCC TGG CAC CTG GTG TTT GCC GCT CGA GGG        768
Arg Lys Leu Leu Leu Thr Pro Trp His Leu Val Phe Ala Ala Arg Gly
                245                 250                 255

CCG GCG CCC GCG CCA GGC GAC TTT GCA CCG GTG TTC GCG CGC CGG CTA        816
Pro Ala Pro Ala Pro Gly Asp Phe Ala Pro Val Phe Ala Arg Arg Leu
                260                 265                 270

CGC GCT GGG GAC TCG GTG CTG GCG CCC GGC GGG GAT GCG CTT CGG CCA        864
Arg Ala Gly Asp Ser Val Leu Ala Pro Gly Gly Asp Ala Leu Arg Pro
            275                 280                 285

GCG CGC GTG GCC CGT GTG GCG CGG GAG GAA GCC GTG GGC GTG TTC GCG        912
Ala Arg Val Ala Arg Val Ala Arg Glu Glu Ala Val Gly Val Phe Ala
        290                 295                 300

CCG CTC ACC GCG CAC GGG ACG CTG CTG GTG AAC GAT GTC CTG GCC TCT        960
Pro Leu Thr Ala His Gly Thr Leu Leu Val Asn Asp Val Leu Ala Ser
305                 310                 315                 320

TGC TAC GCG GTT CTG GAG AGT CAC CAG TGG GCG CAC CGC GCT TTT GCC       1008
Cys Tyr Ala Val Leu Glu Ser His Gln Trp Ala His Arg Ala Phe Ala
                325                 330                 335

CCC TTG AGA CTG CTG CAC GCG CTA GGG GCG CTG CTC CCC GGC GGG GCC       1056
Pro Leu Arg Leu Leu His Ala Leu Gly Ala Leu Leu Pro Gly Gly Ala
            340                 345                 350

GTC CAG CCG ACT GGC ATG CAT TGG TAC TCT CGG CTC CTC TAC CGC TTA       1104
Val Gln Pro Thr Gly Met His Trp Tyr Ser Arg Leu Leu Tyr Arg Leu
        355                 360                 365

GCG GAG GAG CTA CTG GGC                                               1122
Ala Glu Glu Leu Leu Gly
    370

(2) INFORMATION FOR SEQ ID NO: 6:

(i) SEQUENCE CHARACTERISTICS:
        (A) LENGTH: 1188 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: sig peptide
        (B) LOCATION: 1..66
        (C) IDENTIFICATION METHOD: S
```

(A) NAME/KEY: mat peptide
        (B) LOCATION: 67..594
        (C) IDENTIFICATION METHOD: S (xi) SEQUENCE DESCRIPTION: SEQ ID NO: 6:

```
ATG GCT CTC CTG ACC AAT CTA CTG CCC CTG TGC TGC TTG GCA CTT CTG      48
Met Ala Leu Leu Thr Asn Leu Leu Pro Leu Cys Cys Leu Ala Leu Leu
        -20             -15                 -10

GCG CTG CCA GCC CAG AGC TGC GGG CCG GGC CGG GGG CCG GTT GGC CGG      96
Ala Leu Pro Ala Gln Ser Cys Gly Pro Gly Arg Gly Pro Val Gly Arg
     -5              1               5                  10

CGC CGC TAT GCG CGC AAG CAG CTC GTG CCG CTA CTC TAC AAG CAA TTT     144
Arg Arg Tyr Ala Arg Lys Gln Leu Val Pro Leu Leu Tyr Lys Gln Phe
                 15                  20                  25

GTG CCC GGC GTG CCA GAG CGG ACC CTG GGC GCC AGT GGG CCA GCG GAG     192
Val Pro Gly Val Pro Glu Arg Thr Leu Gly Ala Ser Gly Pro Ala Glu
                 30                  35                  40

GGG AGG GTG GCA AGG GGC TCC GAG CGC TTC CGG GAC CTC GTG CCC AAC     240
Gly Arg Val Ala Arg Gly Ser Glu Arg Phe Arg Asp Leu Val Pro Asn
                 45                  50                  55

TAC AAC CCC GAC ATC ATC TTC AAG GAT GAG GAG AAC AGT GGA GCC GAC     288
Tyr Asn Pro Asp Ile Ile Phe Lys Asp Glu Glu Asn Ser Gly Ala Asp
         60                  65                  70

CGC CTG ATG ACC GAA CGT TGT AAG GAA CGG GTG AAC GCT TTG GCC ATT     336
Arg Leu Met Thr Glu Arg Cys Lys Glu Arg Val Asn Ala Leu Ala Ile
 75                  80                  85                  90

GCC GTG ATG AAC ATG TGG CCC GGA GTG CGC CTA CGA GTG ACT GAG GGC     384
Ala Val Met Asn Met Trp Pro Gly Val Arg Leu Arg Val Thr Glu Gly
                     95                 100                 105

TGG GAC GAG GAC GGC CAC CAC GCT CAG GAT TCA CTC CAC TAC GAA GGC     432
Trp Asp Glu Asp Gly His His Ala Gln Asp Ser Leu His Tyr Glu Gly
             110                 115                 120

CGT GCT TTG GAC ATC ACT ACG TCT GAC CGC GAC CGC AAC AAG TAT GGG     480
Arg Ala Leu Asp Ile Thr Thr Ser Asp Arg Asp Arg Asn Lys Tyr Gly
             125                 130                 135

TTG CTG GCG CGC CTC GCA GTG GAA GCC GGC TTC GAC TGG GTC TAC TAC     528
Leu Leu Ala Arg Leu Ala Val Glu Ala Gly Phe Asp Trp Val Tyr Tyr
             140                 145                 150

GAG TCC CGC AAC CAC ATC CAC GTG TCG GTC AAA GCT GAT AAC TCA CTG     576
Glu Ser Arg Asn His Ile His Val Ser Val Lys Ala Asp Asn Ser Leu
155                 160                 165                 170

GCG GTC CGG GCG GGC GGC TGC TTT CCG GGA AAT GCA ACT GTG CGC CTG     624
Ala Val Arg Ala Gly Gly Cys Phe Pro Gly Asn Ala Thr Val Arg Leu
                    175                 180                 185

TGG AGC GGC GAG CGG AAA GGG CTG CGG GAA CTG CAC CGC GGA GAC TGG     672
Trp Ser Gly Glu Arg Lys Gly Leu Arg Glu Leu His Arg Gly Asp Trp
                190                 195                 200

GTT TTG ACG GCC GAT GCG TCA GGC CGG GTG GTG CCC ACG CCG GTG CTG     720
Val Leu Thr Ala Asp Ala Ser Gly Arg Val Val Pro Thr Pro Val Leu
                205                 210                 215

CTC TTC CTG GAC CGG GAC TTG CAG CGC CGG GCT TCA TTT GTG GCT GTG     768
Leu Phe Leu Asp Arg Asp Leu Gln Arg Arg Ala Ser Phe Val Ala Val
            220                 225                 230

GAG ACC GAG TGG CCT CCA CGC AAA CTG TTG CTC ACG CCC TGG CAC CTG     816
Glu Thr Glu Trp Pro Pro Arg Lys Leu Leu Leu Thr Pro Trp His Leu
235                 240                 245                 250

GTG TTT GCC GCT CGA GGG CCG GCG CCC GCG CCA GGC GAC TTT GCA CCG     864
Val Phe Ala Ala Arg Gly Pro Ala Pro Ala Pro Gly Asp Phe Ala Pro
                    255                 260                 265

GTG TTC GCG CGC CGG CTA CGC GCT GGG GAC TCG GTG CTG GCG CCC GGC     912
```

-continued

```
Val Phe Ala Arg Arg Leu Arg Ala Gly Asp Ser Val Leu Ala Pro Gly
        270                 275                 280

GGG GAT GCG CTT CGG CCA GCG CGC GTG GCC CGT GTG GCG CGG GAG GAA       960
Gly Asp Ala Leu Arg Pro Ala Arg Val Ala Arg Val Ala Arg Glu Glu
        285                 290                 295

GCC GTG GGC GTG TTC GCG CCG CTC ACC GCG CAC GGG ACG CTG CTG GTG      1008
Ala Val Gly Val Phe Ala Pro Leu Thr Ala His Gly Thr Leu Leu Val
    300                 305                 310

AAC GAT GTC CTG GCC TCT TGC TAC GCG GTT CTG GAG AGT CAC CAG TGG      1056
Asn Asp Val Leu Ala Ser Cys Tyr Ala Val Leu Glu Ser His Gln Trp
315                 320                 325                 330

GCG CAC CGC GCT TTT GCC CCC TTG AGA CTG CTG CAC GCG CTA GGG GCG      1104
Ala His Arg Ala Phe Ala Pro Leu Arg Leu Leu His Ala Leu Gly Ala
                335                 340                 345

CTG CTC CCC GGC GGG GCC GTC CAG CCG ACT GGC ATG CAT TGG TAC TCT      1152
Leu Leu Pro Gly Gly Ala Val Gln Pro Thr Gly Met His Trp Tyr Ser
            350                 355                 360

CGG CTC CTC TAC CGC TTA GCG GAG GAG CTA CTG GGC                      1188
Arg Leu Leu Tyr Arg Leu Ala Glu Glu Leu Leu Gly
        365                 370
```

(2) INFORMATION FOR SEQ ID NO: 7:

(i) SEQUENCE CHARACTERISTICS:
        (A) LENGTH: 548 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (B) INDIVIDUAL ISOLATE: ARH-77, ATCC CRL-1621

(ix) FEATURE:
        (A) NAME/KEY: sig peptide
        (B) LOCATION: 1..18
        (C) IDENTIFICATION METHOD: S
        (A) NAME/KEY: mat peptide
        (B) LOCATION: 19..546
        (C) IDENTIFICATION METHOD: S (xi) SEQUENCE DESCRIPTION: SEQ ID NO: 7:

```
GCG CTG CCA GCC CAG AGC TGC GGG CCG GGC CGG GGG CCG GTT GGC CGG        48
Ala Leu Pro Ala Gln Ser Cys Gly Pro Gly Arg Gly Pro Val Gly Arg
     -5                  1                   5                 10

CGC CGC TAT GCG CGC AAG CAG CTC GTG CCG CTA CTC TAC AAG CAA TTT        96
Arg Arg Tyr Ala Arg Lys Gln Leu Val Pro Leu Leu Tyr Lys Gln Phe
                15                  20                  25

GTG CCC GGC GTG CCA GAG CGG ACC CTG GGC GCC AGT GGG CCA GCG GAG       144
Val Pro Gly Val Pro Glu Arg Thr Leu Gly Ala Ser Gly Pro Ala Glu
            30                  35                  40

GGG AGG GTG GCA AGG GGC TCC GAG CGC TTC CGG GAC CTC GTG CCC AAC       192
Gly Arg Val Ala Arg Gly Ser Glu Arg Phe Arg Asp Leu Val Pro Asn
        45                  50                  55

TAC AAC CCC GAC ATC ATC TTC AAG GAT GAG GAG AAC AGT GGA GCC GAC       240
Tyr Asn Pro Asp Ile Ile Phe Lys Asp Glu Glu Asn Ser Gly Ala Asp
    60                  65                  70

CGC CTG ATG ACC GAA CGT TGT AAG GAA CGG GTG AAC GCT TTG GCC ATT       288
Arg Leu Met Thr Glu Arg Cys Lys Glu Arg Val Asn Ala Leu Ala Ile
75                  80                  85                  90

GCC GTG ATG AAC ATG TGG CCC GGA GTG CGC CTA CGA GTG ACT GAG GGC       336
Ala Val Met Asn Met Trp Pro Gly Val Arg Leu Arg Val Thr Glu Gly
                95                  100                 105
```

-continued

```
TGG GAC GAG GAC GGC CAC CAC GCT CAG GAT TCA CTC CAC TAC GAA GGC        384
Trp Asp Glu Asp Gly His His Ala Gln Asp Ser Leu His Tyr Glu Gly
            110                 115                 120

CGT GCT TTG GAC ATC ACT ACG TCT GAC CGC GAC CGC AAC AAG TAT GGG        432
Arg Ala Leu Asp Ile Thr Thr Ser Asp Arg Asp Arg Asn Lys Tyr Gly
            125                 130                 135

TTG CTG GCG CGC CTC GCA GTG GAA GCC GGC TTC GAC TGG GTC TAC TAC        480
Leu Leu Ala Arg Leu Ala Val Glu Ala Gly Phe Asp Trp Val Tyr Tyr
            140                 145                 150

GAG TCC CGC AAC CAC ATC CAC GTG TCG GTC AAA GCT GAT AAC TCA CTG        528
Glu Ser Arg Asn His Ile His Val Ser Val Lys Ala Asp Asn Ser Leu
155                 160                 165                 170

GCG GTC CGG GCG GGC GGC TG                                             548
Ala Val Arg Ala Gly Gly
            175
```

(2) INFORMATION FOR SEQ ID NO: 8:

(i) SEQUENCE CHARACTERISTICS:
        (A) LENGTH: 602 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (B) INDIVIDUAL ISOLATE: ARH-77, ATCC CRL-1621

(ix) FEATURE:
        (A) NAME/KEY: 5 UTR
        (B) LOCATION: 1..6
        (C) IDENTIFICATION METHOD: S
        (A) NAME/KEY: sig peptide
        (B) LOCATION: 7..72
        (C) IDENTIFICATION METHOD: S
        (A) NAME/KEY: mat peptide
        (B) LOCATION: 73..600
        (C) IDENTIFICATION METHOD: S (xi) SEQUENCE DESCRIPTION: SEQ ID NO: 8:

```
GTATCC ATG GCT CTC CTG ACC AAT CTA CTG CCC CTG TGC TGC TTG GCA         48
       Met Ala Leu Leu Thr Asn Leu Leu Pro Leu Cys Cys Leu Ala
           -20                 -15                 -10

CTT CTG GCG CTG CCA GCC CAG AGC TGC GGG CCG GGC CGG GGG CCG GTT        96
Leu Leu Ala Leu Pro Ala Gln Ser Cys Gly Pro Gly Arg Gly Pro Val
            -5                  1                   5

GGC CGG CGC CGC TAT GCG CGC AAG CAG CTC GTG CCG CTA CTC TAC AAG       144
Gly Arg Arg Arg Tyr Ala Arg Lys Gln Leu Val Pro Leu Leu Tyr Lys
            10                  15                  20

CAA TTT GTG CCC GGC GTG CCA GAG CGG ACC CTG GGC GCC AGT GGG CCA       192
Gln Phe Val Pro Gly Val Pro Glu Arg Thr Leu Gly Ala Ser Gly Pro
25                  30                  35                  40

GCG GAG GGG AGG GTG GCA AGG GGC TCC GAG CGC TTC CGG GAC CTC GTG       240
Ala Glu Gly Arg Val Ala Arg Gly Ser Glu Arg Phe Arg Asp Leu Val
            45                  50                  55

CCC AAC TAC AAC CCC GAC ATC ATC TTC AAG GAT GAG GAG AAC AGT GGA       288
Pro Asn Tyr Asn Pro Asp Ile Ile Phe Lys Asp Glu Glu Asn Ser Gly
            60                  65                  70

GCC GAC CGC CTG ATG ACC GAA CGT TGT AAG GAA CGG GTG AAC GCT TTG       336
Ala Asp Arg Leu Met Thr Glu Arg Cys Lys Glu Arg Val Asn Ala Leu
            75                  80                  85

GCC ATT GCC GTG ATG AAC ATG TGG CCC GGA GTG CGC CTA CGA GTG ACT       384
Ala Ile Ala Val Met Asn Met Trp Pro Gly Val Arg Leu Arg Val Thr
```

-continued

```
             90                    95                     100
GAG GGC TGG GAC GAG GAC GGC CAC CAC GCT CAG GAT TCA CTC CAC TAC      432
Glu Gly Trp Asp Glu Asp Gly His His Ala Gln Asp Ser Leu His Tyr
105                     110                     115                     120

GAA GGC CGT GCT TTG GAC ATC ACT ACG TCT GAC CGC GAC CGC AAC AAG      480
Glu Gly Arg Ala Leu Asp Ile Thr Thr Ser Asp Arg Asp Arg Asn Lys
                        125                     130                     135

TAT GGG TTG CTG GCG CGC CTC GCA GTG GAA GCC GGC TTC GAC TGG GTC      528
Tyr Gly Leu Leu Ala Arg Leu Ala Val Glu Ala Gly Phe Asp Trp Val
                140                     145                     150

TAC TAC GAG TCC CGC AAC CAC ATC CAC GTG TCG GTC AAA GCT GAT AAC      576
Tyr Tyr Glu Ser Arg Asn His Ile His Val Ser Val Lys Ala Asp Asn
        155                     160                     165

TCA CTG GCG GTC CGG GCG GGC GGC TG                                   602
Ser Leu Ala Val Arg Ala Gly Gly
    170                     175

(2) INFORMATION FOR SEQ ID NO: 9:

(i) SEQUENCE CHARACTERISTICS:
        (A) LENGTH: 575 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (B) INDIVIDUAL ISOLATE: ARH-77, ATCC CRL-1621

(xi) SEQUENCE DESCRIPTION: SEQ ID NO: 9:

C GTG TCG GTC AAA GCT GAT AAC TCA CTG GCG GTC CGG GCG GGC GGC        46
  Val Ser Val Lys Ala Asp Asn Ser Leu Ala Val Arg Ala Gly Gly
  1                   5                     10                      15

TGC TTT CCG GGA AAT GCA ACT GTG CGC CTG TGG AGC GGC GAG CGG AAA      94
Cys Phe Pro Gly Asn Ala Thr Val Arg Leu Trp Ser Gly Glu Arg Lys
                20                      25                      30

GGG CTG CGG GAA CTG CAC CGC GGA GAC TGG GTT TTG ACG GCC GAT GCG      142
Gly Leu Arg Glu Leu His Arg Gly Asp Trp Val Leu Thr Ala Asp Ala
            35                      40                      45

TCA GGC CGG GTG GTG CCC ACG CCG GTG CTG CTC TTC CTG GAC CGG GAC      190
Ser Gly Arg Val Val Pro Thr Pro Val Leu Leu Phe Leu Asp Arg Asp
        50                      55                      60

TTG CAG CGC CGG GCT TCA TTT GTG GCT GTG GAG ACC GAG TGG CCT CCA      238
Leu Gln Arg Arg Ala Ser Phe Val Ala Val Glu Thr Glu Trp Pro Pro
65                      70                      75

CGC AAA CTG TTG CTC ACG CCC TGG CAC CTG GTG TTT GCC GCT CGA GGG      286
Arg Lys Leu Leu Leu Thr Pro Trp His Leu Val Phe Ala Ala Arg Gly
80                      85                      90                      95

CCG GCG CCC GCG CCA GGC GAC TTT GCA CCG GTG TTC GCG CGC CGG CTA      334
Pro Ala Pro Ala Pro Gly Asp Phe Ala Pro Val Phe Ala Arg Arg Leu
                100                     105                     110

CGC GCT GGG GAC TCG GTG CTG GCG CCC GGC GGG GAT GCG CTT CGG CCA      382
Arg Ala Gly Asp Ser Val Leu Ala Pro Gly Gly Asp Ala Leu Arg Pro
            115                     120                     125

GCG CGC GTG GCC CGT GTG GCG CGG GAG GAA GCC GTG GGC GTG TTC GCG      430
Ala Arg Val Ala Arg Val Ala Arg Glu Glu Ala Val Gly Val Phe Ala
        130                     135                     140

CCG CTC ACC GCG CAC GGG ACG CTG CTG GTG AAC GAT GTC CTG GCC TCT      478
Pro Leu Thr Ala His Gly Thr Leu Leu Val Asn Asp Val Leu Ala Ser
145                     150                     155
```

```
TGC TAC GCG GTT CTG GAG AGT CAC CAG TGG GCG CAC CGC GCT TTT GCC      526
Cys Tyr Ala Val Leu Glu Ser His Gln Trp Ala His Arg Ala Phe Ala
160                 165                 170                 175

CCC TTG AGA CTG CTG CAC GCG CTA GGG GCG CTG CTC CCC GGC GGG GCC      574
Pro Leu Arg Leu Leu His Ala Leu Gly Ala Leu Leu Pro Gly Gly Ala
            180                 185                 190

G                                                                    575
```

(2) INFORMATION FOR SEQ ID NO: 10:

(i) SEQUENCE CHARACTERISTICS:
        (A) LENGTH: 230 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (B) INDIVIDUAL ISOLATE: ARH-77, ATCC CRL-1621

(ix) FEATURE:
        (A) NAME/KEY: 3 UTR
        (B) LOCATION: 218..230
        (C) IDENTIFICATION METHOD: S (xi) SEQUENCE DESCRIPTION: SEQ ID NO: 10:

```
G TTC GCG CCG CTC ACC GCG CAC GGG ACG CTG CTG GTG AAC GAT GTC        46
  Phe Ala Pro Leu Thr Ala His Gly Thr Leu Leu Val Asn Asp Val
  1               5                   10                  15

CTG GCC TCT TGC TAC GCG GTT CTG GAG AGT CAC CAG TGG GCG CAC CGC      94
Leu Ala Ser Cys Tyr Ala Val Leu Glu Ser His Gln Trp Ala His Arg
            20                  25                  30

GCT TTT GCC CCC TTG AGA CTG CTG CAC GCG CTA GGG GCG CTG CTC CCC     142
Ala Phe Ala Pro Leu Arg Leu Leu His Ala Leu Gly Ala Leu Leu Pro
                35                  40                  45

GGC GGG GCC GTC CAG CCG ACT GGC ATG CAT TGG TAC TCT CGG CTC CTC     190
Gly Gly Ala Val Gln Pro Thr Gly Met His Trp Tyr Ser Arg Leu Leu
            50                  55                  60

TAC CGC TTA GCG GAG GAG CTA CTG GGC TGAGCGTCCC AGG                  230
Tyr Arg Leu Ala Glu Glu Leu Leu Gly
            65                  70
```

(2) INFORMATION FOR SEQ ID NO: 11:

(i) SEQUENCE CHARACTERISTICS:
        (A) LENGTH: 522 base pairs
        (B) TYPE: nucleic acid
        (C) STRANDEDNESS: double
        (D) TOPOLOGY: linear (ii) MOLECULE TYPE: cDNA (vi) ORIGINAL SOURCE:
        (A) ORGANISM: human
        (B) INDIVIDUAL ISOLATE: A549, ATCC CRL-185

(ix) FEATURE:
        (A) NAME/KEY: mat peptide
        (B) LOCATION: 1..522
        (C) IDENTIFICATION METHOD: S (xi) SEQUENCE DESCRIPTION: SEQ ID NO: 11:

```
TGC GGA CCG GGC AGG GGG TTC GGG AAA AGG AGG CAC CCC AAA AAG CTG      48
Cys Gly Pro Gly Arg Gly Phe Gly Lys Arg Arg His Pro Lys Lys Leu
1               5                   10                  15

ACC CCT TTA GCC TAC AAG CAG TTT ATC CCC AAT GTG GCC GAA AAG ACC      96
Thr Pro Leu Ala Tyr Lys Gln Phe Ile Pro Asn Val Ala Glu Lys Thr
```

```
            Thr Pro Leu Ala Tyr Lys Gln Phe Ile Pro Asn Val Ala Glu Lys Thr
                        20                  25                  30

CTA GGC GCC AGC GGA AGG TAT GAA GGG AAG ATC TCC AGA AAC TCC GAG            144
Leu Gly Ala Ser Gly Arg Tyr Glu Gly Lys Ile Ser Arg Asn Ser Glu
            35                  40                  45

CGA TTT AAG GAA CTC ACC CCC AAT TAC AAC CCC GAC ATC ATA TTT AAG            192
Arg Phe Lys Glu Leu Thr Pro Asn Tyr Asn Pro Asp Ile Ile Phe Lys
        50                  55                  60

GAT GAA GAA AAC ACC GGA GCG GAC AGG CTG ATG ACT CAG AGG TGT AAG            240
Asp Glu Glu Asn Thr Gly Ala Asp Arg Leu Met Thr Gln Arg Cys Lys
65                  70                  75                  80

GAC AAG TTG AAC GCT TTG GCC ATC TCG GTG ATG AAC CAG TGG CCA GGA            288
Asp Lys Leu Asn Ala Leu Ala Ile Ser Val Met Asn Gln Trp Pro Gly
                85                  90                  95

GTG AAA CTG CGG GTG ACC GAG GGC TGG GAC GAA GAT GGC CAC CAC TCA            336
Val Lys Leu Arg Val Thr Glu Gly Trp Asp Glu Asp Gly His His Ser
            100                 105                 110

GAG GAG TCT CTG CAC TAC GAG GGC CGC GCA GTG GAC ATC ACC ACG TCT            384
Glu Glu Ser Leu His Tyr Glu Gly Arg Ala Val Asp Ile Thr Thr Ser
        115                 120                 125

GAC CGC GAC CGC AGC AAG TAC GGC ATG CTG GCC CGC CTG GCG GTG GAG            432
Asp Arg Asp Arg Ser Lys Tyr Gly Met Leu Ala Arg Leu Ala Val Glu
    130                 135                 140

GCC GGC TTC GAC TGG GTG TAC TAC GAG TCC AAG GCA CAT ATC CAC TGC            480
Ala Gly Phe Asp Trp Val Tyr Tyr Glu Ser Lys Ala His Ile His Cys
145                 150                 155                 160

TCG GTG AAA GCA GAG AAC TCG GTG GCG GCC AAA TCG GGA GGC                    522
Ser Val Lys Ala Glu Asn Ser Val Ala Ala Lys Ser Gly Gly
                165                 170             174

(2) INFORMATION FOR SEQ ID NO: 12:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 12:

GCCAGGGTGT GAGCAACAGT                                                       20

(2) INFORMATION FOR SEQ ID NO: 13:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 13:

TGTGCTGCTT GGCACTCTTG                                                       20

(2) INFORMATION FOR SEQ ID NO: 14:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 14:

CCGTGGCATT TCCCGGAAAG                                                       20
```

```
(2) INFORMATION FOR SEQ ID NO: 15:

(i) SEQUENCE CHARACTERISTICS:
          (A) LENGTH: 18 base pairs
          (B) TYPE: nucleic acid
          (C) STRANDEDNESS: single
          (D) TOPOLOGY: linear (xi) SEQUENCE DESCRIPTION: SEQ ID NO: 15:

GTATCCATGG CTCTCCTG                                            18

(2) INFORMATION FOR SEQ ID NO: 16:

(i) SEQUENCE CHARACTERISTICS:
          (A) LENGTH: 26 base pairs
          (B) TYPE: nucleic acid
          (C) STRANDEDNESS: single
          (D) TOPOLOGY: linear (xi) SEQUENCE DESCRIPTION: SEQ ID NO: 16:

GCCTCGAGGT ATCCATGGCT CTCCTG                                   26

(2) INFORMATION FOR SEQ ID NO: 17:

(i) SEQUENCE CHARACTERISTICS:
          (A) LENGTH: 28 base pairs
          (B) TYPE: nucleic acid
          (C) STRANDEDNESS: single
          (D) TOPOLOGY: linear (xi) SEQUENCE DESCRIPTION: SEQ ID NO: 17:

GCGCGGCCGC TCAGCCGCCC GCCCGGAC                                 28

(2) INFORMATION FOR SEQ ID NO: 18:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO: 18:

CGTGTCGGTC AAAGCTGATA                                          20

(2) INFORMATION FOR SEQ ID NO: 19:

(i) SEQUENCE CHARACTERISTICS:
          (A) LENGTH: 20 base pairs
          (B) TYPE: nucleic acid
          (C) STRANDEDNESS: single
          (D) TOPOLOGY: linear (xi) SEQUENCE DESCRIPTION: SEQ ID NO: 19:

ATGCATTCCA GTCGGCTGGA                                          20

(2) INFORMATION FOR SEQ ID NO: 20:

(i) SEQUENCE CHARACTERISTICS:
          (A) LENGTH: 56 base pairs
          (B) TYPE: nucleic acid
          (C) STRANDEDNESS: single
          (D) TOPOLOGY: linear (xi) SEQUENCE DESCRIPTION: SEQ ID NO: 20:

AAGGATCCGT CGACAAGCTT AATACGACGA ATTCTGGAGT TTTTTTTTTT TTTTTT   56

(2) INFORMATION FOR SEQ ID NO: 21:
```

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO: 21:

GGCTTCGACT GGGTCTACTA                                               20

(2) INFORMATION FOR SEQ ID NO: 22:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 22:

AAGGATCCGT CGACAAG                                                  17

(2) INFORMATION FOR SEQ ID NO: 23:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 23:

ATGCGCTTCG GCCAGCG                                                  17

(2) INFORMATION FOR SEQ ID NO: 24:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 24:

GACAAGCTTA ATACGAC                                                  17

(2) INFORMATION FOR SEQ ID NO: 25:

(i) SEQUENCE CHARACTERISTICS:
        (A) LENGTH: 17 base pairs
        (B) TYPE: nucleic acid
        (C) STRANDEDNESS: single
        (D) TOPOLOGY: linear (xi) SEQUENCE DESCRIPTION: SEQ ID NO: 25:

GTTCGCGCCG CTCACCG                                                  17

(2) INFORMATION FOR SEQ ID NO: 26:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 26:

TACGACGAAT TCTGGAGT                                                 18

(2) INFORMATION FOR SEQ ID NO: 27:

```
        (i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO: 27:

CCCGGGAATT CATTGCGGGC CGGGCCGGGG GCCG                                       34

(2) INFORMATION FOR SEQ ID NO: 28:

(i) SEQUENCE CHARACTERISTICS:
            (A) LENGTH: 34 base pairs
            (B) TYPE: nucleic acid
            (C) STRANDEDNESS: single
            (D) TOPOLOGY: linear (xi) SEQUENCE DESCRIPTION: SEQ ID NO: 28:

ACGATGAATT CTCAGCCGCC CGCCCGGACC GCCA                                       34

(2) INFORMATION FOR SEQ ID NO: 29:

(i) SEQUENCE CHARACTERISTICS:
            (A) LENGTH: 6 amino acids
            (B) TYPE: amino acid
            (C) STRANDEDNESS: single
            (D) TOPOLOGY: linear (xi) SEQUENCE DESCRIPTION: SEQ ID NO: 29:

Gly Ser Pro Gly Ile His
 1               5

(2) INFORMATION FOR SEQ ID NO: 30:

(i) SEQUENCE CHARACTERISTICS:
            (A) LENGTH: 33 base pairs
            (B) TYPE: nucleic acid
            (C) STRANDEDNESS: single
            (D) TOPOLOGY: linear (xi) SEQUENCE DESCRIPTION: SEQ ID NO: 30:

CCCGGGAATT CATTGCGGAC CGGGCAGGGG GTT                                        33

(2) INFORMATION FOR SEQ ID NO: 31:

(i) SEQUENCE CHARACTERISTICS:
            (A) LENGTH: 32 base pairs
            (B) TYPE: nucleic acid
            (C) STRANDEDNESS: single
            (D) TOPOLOGY: linear (xi) SEQUENCE DESCRIPTION: SEQ ID NO: 31:

ACGATGAATT CTCAGCCTCC CGATTTGGCC GC                                         32
```

MP121, A GROWTH/DIFFERENTIATION FACTOR OF THE TGF-β FAMILY

CROSS-REFERENCE TO RELATED APPLICATIONS

This application is a division of U.S. patent application Ser. No. 09/218,176 filed Dec. 22, 1998, now U.S. Pat. No. 6,171,584, which in turn is a continuation of U.S. patent application Ser. No. 08/679,048 filed Jul. 12, 1996, now abandoned, which in turn is a continuation-in-part of U.S. patent application Ser. No. 08/482,577, filed Jun. 7, 1995, now U.S. Pat. No. 5,807,713, which in turn is a continuation-in-part of U.S. patent application Ser. No. 08/289,222 filed Aug. 12, 1994, now U.S. Pat. No. 6,120,760, which in turn is a continuation-in-part of PCT international application No. PCT/EP93/00350 filed Feb. 12, 1993. The disclosures of the prior applications are incorporated by reference herein in their entirety.

DESCRIPTION

The present invention concerns a new growth/differentiation factor of the TGF-β family and DNA sequences coding therefor.

The BMP-, TGF- and inhibin-related proteins are members of the TGF-β family of growth factors (Roberts and Sporn, Handbook of Experimental Pharmacology 95, 419–472 (1990)). They are relevant for a wide range of medical therapeutic methods and applications. These factors are suitable for methods relating to wound healing and tissue regeneration. Moreover several members of the TGF-β family induce tissue growth for example the growth of bones.

Wozney (Progress in Growth Factor Research 1 (1989), 267–280) and Vale et al. (handbook of Experimental Pharmacology 95 (1990), 211–248) describe various growth factors for example those which are related to the BMP and the activin/inhibin group. The members of this group have significant structural similarities. The precursor of the protein is composed of an amino-terminal signal sequence, a propeptide sequence and a carboxy-terminal sequence of 110 to 140 amino acids which is cleaved from the precursor and represents the mature protein. Furthermore its members are defined by an amino acid sequence homology. The mature protein contains the sequences that are conserved most, in particular seven cysteine residues which are conserved among the family members. The TGF-β-like proteins are multifunctional, hormonally active growth factors. They also have related biological activities for example chemotactic attraction of cells, promotion of cell differentiation and tissue-inducing capabilities. EP 0 222 491 A1 discloses sequences of inhibin alpha and beta chains.

On the whole the proteins of the TGF-β family show differences in their structure which leads to considerable variations in their exact biological function. In addition they are found in a wide range of different types of tissues and stages of development. As a consequence they may be different with regard to their exact function e.g. the required cellular physiological environment, their left span, their target areas, their requirements for auxiliary factors and their resistance to degradation. Although numerous proteins that show tissue-inductive potential have been described, their natural functions in the organism and—even more importantly—their medical relevance still has to be researched in detail. It can in all probability be assumed that there are still unknown members of the TGF-β family which are of importance for the differentiation/induction of various types of tissue. However, a major difficulty in the isolation of these new TGF-β-like proteins is that their functions cannot yet be described precisely enough to develop a highly discriminating bioassay. On the other hand the expected nucleotide sequence homology to known members of the family is too small to enable screening by classical nucleic acid hybridization techniques. Nevertheless the further isolation and characterization of new TGF-β-like proteins is urgently required in order to provide further inducing and differentiation proteins which fulfil all medical requirements. These factors could be used medically in healing injuries and treating degenerative diseases of various tissues.

A nucleotide and amino acid sequence for the TGF-β protein MP121 is given in the patent application PCT/ED93/00350 in which a major part of the sequence corresponding to the mature protein is stated. The complete sequence of the propeptide MP121 is not disclosed.

The underlying object of the present invention is to provide DNA sequences which code for new members of the TGF-β protein family with mitogenic and/or differentiation-inductive potential. The object of the present invention is in particular to provide the complete DNA and amino acid sequence of the TGF protein MP121.

This object is achieved by a DNA molecule that codes for a protein of the TGF-β family and which comprises (a) the part coding for the mature protein and if necessary further functional parts of the nucleotide sequence shown in SEQ ID NO. 1, (b) a nucleotide sequence corresponding to the sequence from (a) within the scope of the degeneracy of the genetic code, (c) a nucleotide sequence corresponding to an allelic derivative of one of the sequences from (a) and (b) or (d) a sequence which differs from sequence (a) due to the fact that it originates from other vertebrates (e) a sequence hybridizing with one of the sequences from (a), (b), (c) or (d)

provided that a DNA molecule according to (e) contains at least the part coding for a mature protein of the TGF-β family.

Further embodiments of the present invention concern the subject matter of claims 2 to 10. Other features and advantages of the invention emerge from the description of the preferred embodiments. The sequence protocols and drawings are now briefly described.

SEQ ID NO. 1 shows the complete nucleotide sequence of the DNA coding for the human TGF-β protein MP121. The ATG start codon begins at nucleotide 128. The start of the complete mature protein particularly preferably begins at nucleotide 836.

SEQ ID NO. 2 shows the complete amino acid sequence of the preproprotein of the human TGF-β protein MP121 which was derived from the nucleotide sequence shown in SEQ ID NO. 1. The start of the mature protein is preferably in the region of amino acids 217–240, particularly preferably at amino acid 236 or 237 and most preferably at amino acid 237.

SEQ ID NO. 3 shows the complete nucleotide sequence of the DNA coding for the TGF-β protein MP121 from the mouse. The coding region begins at the ATG start codon at nucleotide 131 and ends at the stop codon beginning at position 1187. The start of the mature protein preferably begins at nucleotide 839. A ca. 5.5 kb large intron is located in the genomic DNA between position 446 and 447.

SEQ ID NO. 4 shows the complete amino acid sequence of the preprotein of the TGF-β protein MP121 from the mouse which has been derived from the nucleotide sequence shown in SEQ ID NO. 3. The mature protein begins in the region of amino acids 217–240 in analogy to the human MP121 of SEQ ID NO. 2. It is most preferred when the mature protein starts at amino acid 237 so that the mature part consists of 116 amino acids as in the human MP121. Members of the TGF-β family are frequently cleaved behind a RXXR cleavage site in order to separate the mature part from the precursor (see Özkaynak et al., J. Biol. Chem. 267, 25220–25227 (1992) and the literature cited therein). In the case of MP121 from the mouse it is also conceivable that the beginning of the mature protein is at least sometimes at amino acid 236.

SEQ ID NOS:5 and 6 show the nucleotide sequence of the human MP121 gene at the exon/intron junctions.

BRIEF DESCRIPTION OF THE FIGURES

FIG. 1 shows a comparison of the amino acid sequences of human MP121 (SEQ ID NO:7) with some members of the TGF-β family (inhibin α and β chains) (SEQ ID NOS:8–10) starting at the first of the seven conserved cysteine residues. * denotes that the amino acid is the same in all compared proteins; + denotes that the amino acid corresponds in at least one of the proteins compared to human MP121.

FIG. 2 shows the nucleotide sequences (SEQ ID NOS: 11–32) of the oligonucleotide primers which were used in the present invention and a comparison of these sequences with known members of the TGF-β family. M denotes A or C, S denotes C or G, R denotes A or G and K denotes G or T. FIG. 2a shows the sequence of primer OD-, (SEQ ID NO:11). FIG. 2b shows the sequence of primer OID (SEQ ID NO:22).

Figure 3:
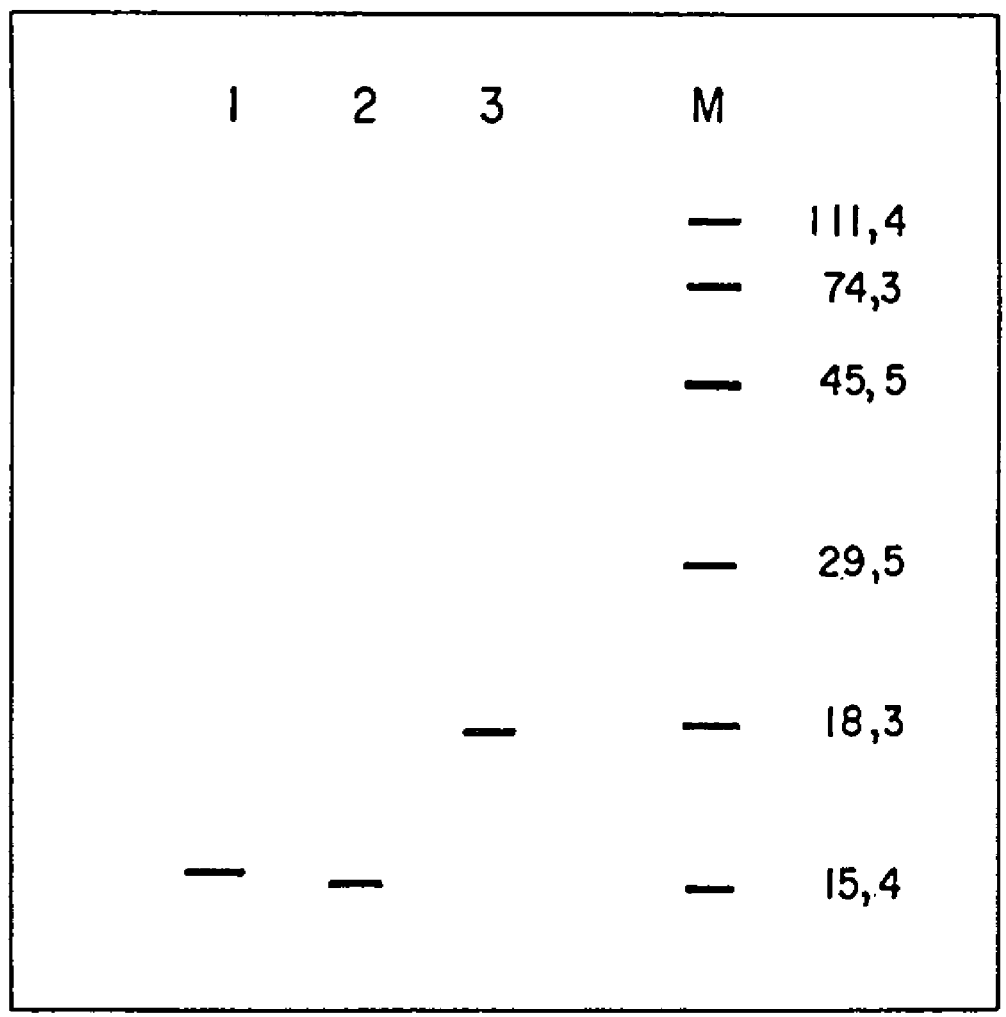
FIG. 3 shows a diagram of a Western blot using chicken antibodies against human MP121, Lane 1 shows E. coli cells transformed with pBP4MP121His under reducing conditions (1% β-mercaptoethanol). Lane 2 shows cell culture supernatant of NIH-3T3 cells after infection with recombinant viruses (with inserted MP121 cDNA) under reducing conditions (1% β-mercaptoethanol). Lane 3 shows cell culture supernatant of NIH-3T3 cells after infection with recombinant viruses (with inserted MP121 cDNA) under non-reducing conditions. Lane M shows prestained protein molecular weight markers having the stated apparent molecular weights (Gibco BRL #26041-020).
Figure 4:
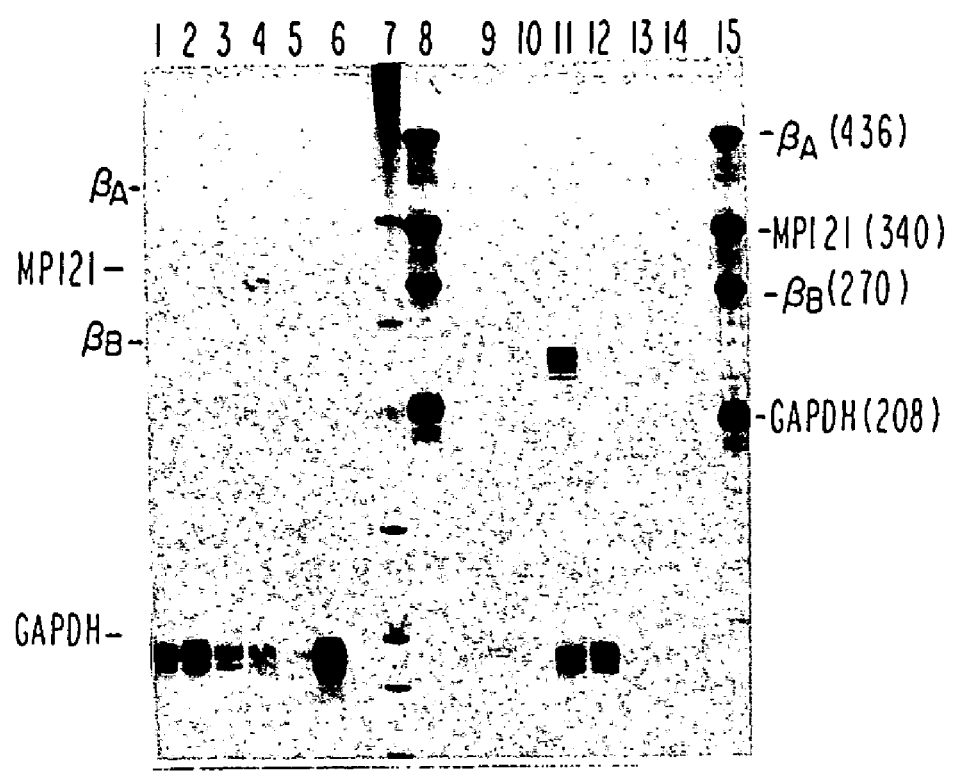
FIG. 4 shows the expression of MP121 compared to active $\beta_A$ and $\beta_B$ in various mouse tissues and is an autoradiogram after gel analysis of an RNase protection assay using specific probes against activin βA (βA), activin βB (βB), MP121 and against GAPDH for the control. Total RNA was tested which has been isolated from various mouse tissues (Lane 1: brain; Lane 2: heart, Lane 3: kidney, Lane 4: liver, Lane 5: lung, Lane 6: muscle, Lane 9: ovary, Lane 10: spleen, Lane 11: testes) from embryonic stem cells (Lane 12: C17) and from yeast (Lane 13) as a control. No RNA was used in Lane 14 as a control. The unprotected antisense RNA probes used for the hybridization are applied in lanes 8 and 15 and the expected fragment size is indicated in brackets in the right margin. The bands of the protected fragments are labeled in the left margin. PRB322 restricted with Msp 1 (Biolabs #303) and end-labeled with γ-32p-ATP (Amesham) was used as the marker (Lane 7).

Within the scope of the present invention the term "mature protein" also encompasses functional partial regions of the complete protein which exhibit essentially the same biological activity and preferably those partial regions which includes at least the region of the seven cysteines that are conserved in the TGF-β family. In this case it is in particular possible that the N-terminus of the mature protein is slightly modified i.e. deviates from the sequences shown in SEQ ID NO.2 and 4. In this connection additional amino acids, which do not influence the functionality of the protein, may be present or amino acids may be absent provided that in this case the functionality is also not impaired. However, it is preferred that the human protein and the mouse protein contain all amino acids starting with amino acid 237 of the amino acid sequence shown in SEQ ID NO.2 and SEQ ID NO.4. It is already known from other family members of the TGF-β family that the attachment of additional amino acids to the N-terminus of the mature protein does not influence the activity wherein inter alia 6 additional histidines were attached to the N-terminus.

Therefore the present invention encompasses the part coding for the mature protein in accordance with the above-mentioned definition and if necessary, further functional parts of the nucleotide sequence shown in SEQ ID NO. 1 as well as sequences that correspond to this sequence within the scope of the degeneracy of the genetic code and allelic derivatives of such sequences. Furthermore the present invention also encompasses DNA sequences which code for a protein of the TGR-β family which were obtained from other mammals and which have a sequence that deviates slightly due to their origin but which, however, code for proteins having in principle the same biological function and also sequences that differ only slightly. Such sequences correspond to one another to a very large extent as can be seen by comparing SEQ ID NO. 1 and NO. 3.

In addition the present invention also covers sequences hybridizing with such sequences provided that such a DNA molecule at least completely contains the part coding for a mature protein of the TGF-β family (according to the above definition) and the biological activity is retained.

The term "functional part" within the sense of the present invention denotes a protein part which is capable of acting for example as a signal peptide, propeptide or mature protein moiety i.e. it fulfills at least one of the biological functions of the natural parts of MP121.

In the case of the preferred human MP121 the region coding for the mature part of the protein preferably extends from nucleotide 836 to the stop codon which begins at nucleotide 1184 of the sequence shown in SEQ ID NO. 1. If necessary, the DNA molecule can include further functional parts of the sequence shown in SEQ ID NO. 1 namely the nucleotide sequences coding for the signal or/and propeptide part. It is particularly preferred that the DNA molecule comprises the sequence for the signal and propeptide part and the mature protein part i.e. nucleotides 128 to 1184 of the sequence shown in SEQ ID NO. 1. In the case of the preferred mouse MP121 the region coding for the mature part of the protein preferably extends from nucleotide 839 to the stop codon starting at position 1187 of the sequence shown in SEQ ID NO. 3. if desired the DNA molecule can also include further functional parts of the sequence shown in SEQ ID NO. 3 i.e. if desired nucleotide sequences coding for the signal or/and propeptide part.

On the other hand the DNA molecules can also include functional signal or/and propeptide parts of other proteins e.g. of proteins with the cysteine knot motif (Cell, vol. 73 (1993), p. 421–424) and in particular of other proteins of the TGF-β family e.g. the abovementioned activin/inhibin or BMP proteins especially also MP52 (see PCT/EP94/02630) in addition to the part coding for the mature protein. The respective nucleotide sequences can be found in the aforementioned references to the disclosure of which reference is herewith made. In this case it is important that the correct reading frame for the mature protein is preserved. Depending in which host cells expression takes place, the presence of another signal sequence or/and of another propeptide part may positively influence the expression. The exchange of propeptide parts by corresponding parts of other proteins is described for example in Mol. Endocrinol. 5, (1991), 149 . 155 and Proc. Natl. Acad. Sci. USA 90 (1993), 2905–2909.

Although the allelic, degenerated and hybridizing sequences and sequences derived from other vertebrates which are covered by the present invention have structural differences due to slight changes in the nucleotide or/and amino acid sequence, proteins which are coded by such sequences still essentially have the same useful properties which enable them to be used in essentially the same medical fields of application.

According to the present invention the term "hybridization" denotes the usual hybridization conditions, preferably conditions with a salt concentration of 6x SSC at 62 to 66° C. followed by a one hour wash with 0.6×SSC, 0.1% SDS at 62 to 66° C.

Preferred embodiments of the present invention are DNA sequences as defined above which are obtainable from vertebrates, preferably mammals such as pigs, cows and rodents such as rats or mice and in particular from primates such as humans or which are copied from corresponding sequences.

A particularly preferred embodiment of the present invention are the sequences shown in SEQ ID NO. 1 and 3 and denoted human or mouse MP121 sequences. The transcripts of MP121 were obtained from liver tissue and code for a protein which shows a considerable amino acid homology to the mature part of the inhibitin/activin-like proteins (see FIG. 1). The protein sequences of human α-inhibin, inhibin $β_A$ (activin $β_A$) and inhibin $β_B$ (activin $β_B$) are described by Mason et al. (Biochem. Biophys. Res. Com. 135, 957–964 (1986). Some typical sequence homologies which are specific for known inhibitin sequences were also found in the propeptide part of MP121 while other parts of the propeptide of MP121 show considerable differences to inhibin propeptides.

However previous findings show that there are differences between the pattern of expression of MP121 and that of the activins. While activins are mainly expressed in the gonads (activin $β_A$ in ovaries and activin $β_B$ in testes and ovaries), MP121 is mainly expressed in the liver. However up to now the sensitivity of the experiments has not been sufficient to also detect a slight expression. Thus in the case of activins it has for example been described in the literature that expression can also be detected outside the gonads in various rat tissues in adult animals (Meunier et al., Proc. Natl. Acad. Sci. USA 85, 247–251 (1988)) as well as during embryonic development (Roberts et al., Endocrinology 128, 3122–3129 (1991)). Therefore it is also possible that expression of MP121 in other tissues may yet be detected.

Because of the predominant expression of MP121 in liver the expression in one typical cell type of the liver was investigated in more detail. It was shown that the mRNA is expressed abundantly in cultured primary rat hepatocytes as well as in liver cell lines such as HepG2 (ATCC HB 8065). The expression in primary cells is markedly reduced by EGF (Epidermal Growth Factor) treatment after 60 hours. This pattern is completely different compared to activin βA mRNA, which is barely expressed in hepatocytes but increased drastically after ECF treatment (Yasuda et al., J. Clin.Invest. Vol.92, 1491–1496 (1993)). Likewise, the expression of activin βA mRNA and MP121 mRNA is reciprocal in remnant rat liver after 70% hepatectomy. MP121 mRNA is detected significantly before hepatectomy but is markedly decreased after 12 hours or later, whereas the mRNA for activin βA is quite low before but elevated 12 hours or later after hepatectomy. Therefore MP121 seems to have a big influence on the ability of the liver to regenerate and proliferate. The control of MP121 mRNA expression and/or the amount of MP121 protein in liver can be of significance for treatment of liver carcinomas, liver injuries or diseases such as for example cirrhotic liver.

In addition the present invention concerns a vector which contains at least one copy of a DNA molecule according to the invention. In such a vector the DNA sequence according to the invention is preferably linked operatively with an expression control sequence. Such vectors are suitable for producing TGF-β-like proteins in stably or transiently-transformed cells. Various animal, plant, fungal and bacterial systems can be used for the transformation and the subsequent culture. The vectors according to the invention preferably contain sequences necessary for replication in the host cell and they are autonomously replicable. In addition the use of vectors is preferred which contain selectable marker genes by which means the transformation of a host cell can be detected.

Furthermore the invention concerns a host cell which is transformed with a DNA according to the invention or with a vector according to the invention. Examples of suitable host cells include various eukaryotic and prokaryotic cells such as E. coli, insect cells, plant cells, mammalian cells and fungi such as yeast.

In addition the invention concerns a protein of the TGF-β family which is coded by a DNA sequence according to claim 1. The protein according to the invention preferably has the amino acid sequence shown in SEQ ID NO. 2 or in SEQ ID NO. 4 or if desired functional parts thereof (as defined above) and exhibits biological properties such as tissue-inductive properties which may be relevant for a therapeutic application. The above-mentioned features of the protein can vary depending on the formation of homodimers or heterodimers with other proteins having the "cystine knot motif" and in particular TGF-β proteins. Such structures may also prove to be suitable for clinical applications and thus are also a subject matter of the present invention. Preferred heterodimers include heterodimers composed of a monomer of the protein according to the invention and monomers of the α, $β_A$ or $β_B$ inhibin chains. The properties resulting from heterodimer formation can be shifted more towards the properties of activin or inhibins. If for example a heterodimer is formed with inhibin α proteins or with other inhibin β proteins, then it is assumed that the MP12/inhibin (α chain) or MP 121/activin ($β_A$ or $β_B$ chain) heterodimer can inhibit or activate the formation of follicle-stimulating hormone (FSH). MP121/activin heterodimers may also for example influence masoderm development. Furthermore, it is expected that heterodimeric forms with a member of the BMP group of TGF-β proteins lead to an amplification of BMP-like activities such as for example the ability to induce or promote bone formation, formation of cartilage of formation of connective tissue.

The invention therefore also concerns heterodimeric proteins of a protein of the TGF-β family according to the invention which is coded by a DNA sequences as claimed in claim 1 containing a monomer of a protein with the "cystine knot motif" preferably of another member of the TGF-β family. Similar heterodimeric proteins are described in WO93/09229, EP 0 626 451 A2 and J. Biol. Chem. 265 (1990), 13198–13205.

In addition the invention concerns chimeric proteins which have functional derivatives or parts of a protein coded by a DNA sequence according to the invention preferably as shown in SEQ ID NO.2 or SEQ ID NO.4, in particular functional parts of the mature protein and additionally parts of another protein. In this case the other protein can also be a protein with a "cystine knot motif" which is preferably also a member of the TGF-β family such as e.g. especially MP52 (PCT/EP94/02630). However, parts of a complete different protein can also be present e.g. receptor-binding domains of proteins which lend the initial MP121 protein another specificity.

The biological properties of the proteins according to the invention, preferably MP121, can be determined for example in assays according to Wrana et al., (Cell 71, 1003–1014 (1992)), Ling et al. (Proc. Natl. Acad. of Science, 82, 7217–7221 (1985)), Takuwa et al. (Am. J. Physiol. 257, E797–E803 (1989)), Fann and Patterson (Proc. Natl. Acad. of Science, 91, 43–47 (1994)), Broxmeyer et al. (Proc. Natl. Acad. of Science, 85, 9052–9056 (1988)), Green et al. (Cell, 71, 731–739 (1992)) or Partridge et al. (Endocrinology, 108, 213–219 (1981)) or Krieglstein et al. (EMBO J. 14, 736–742 (1995)).

Figure 5:
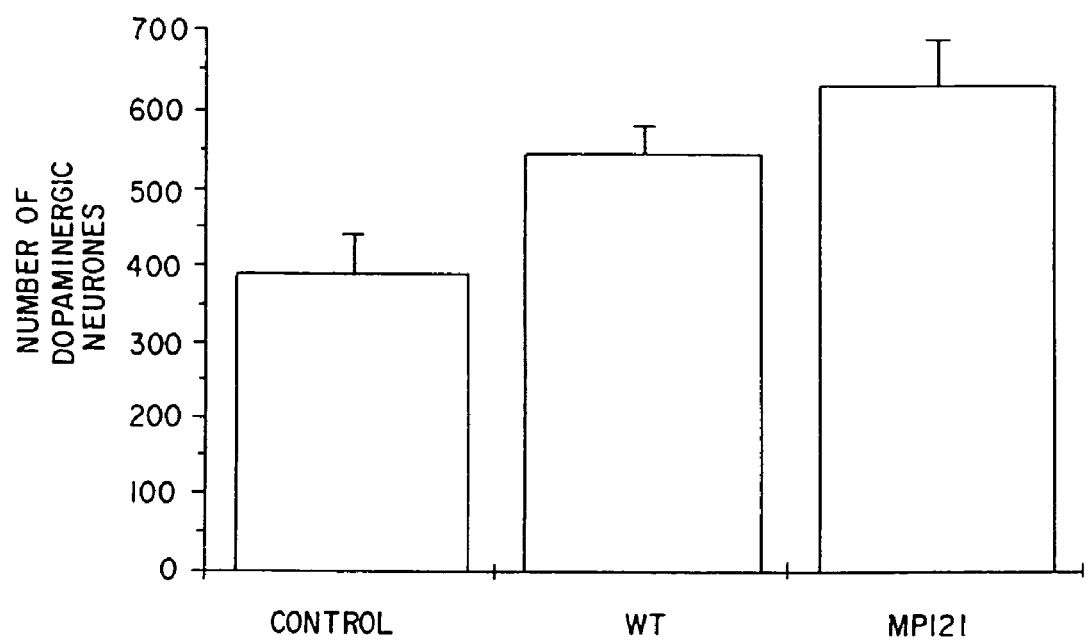
FIG. 5 shows a positive influence on the survival of dopaminergic neurons by treatment with partially purified MP121. The number of TH-immunoreactive dopaminergic neurons surviving after isolation from the mesencephalon of rat embryos (E14) after 8 days culture is shown. The effect of 20 ng/ml partially purified MP121 was tested compared to the equivalent amount of partially purified control supernatant (wt) as well as untreated neurons (control: medium containing 0.3% acetonitrile). The mean±SEM from a triple determination is shown.

Activin A and TGF-β1, TGF-β2 and TGF-β3 have been described to promote survival of dopaminergic neurones in vitro (Krieglstein et al., EMBO J. 14, 736–742 (1995) and Krieglstein et al., Neuroscience 63, 1189–1196 (1994)). In the case of partially purified MP121 it could be shown that the survival of dopaminergic neurones in a 8-day culture is promoted to a greater extent than by the influence of the control supernatant (FIG. 5).

During the development of the visual system a projection of axons from the retinal ganglion cells to the special regions in the brain is established. It was shown by several groups that soluble factors isolated from visual areas of the brain can trophically stimulate retinal ganglion cells (Nurcombe, V. & Bennett, M. R., Exp. Brain Res. 44, 249–258 (1981), Hyndman, A. G., Adler, R., Dev. Neurosci. 5, 40–53 (1982), Turner, J. E. et al., Dev. Brain Res. 6, 77–83 (1983), Carri, N. C. & Ebendal, T., Dev. Brain Res. 6, 219–229 (1983)). The formation of nerve fibre fascicleu, which most likely represent optic axons stemming from the retinal ganglion cells, depends on neurotrophic factors. Using MP121, a strong stimulation of retinal nerve fibre outgrowth in explant cultures of the embryonic chicken retina was evident as shown in Tab.1 and FIG. 7. During this experiments, other members of the TGF-β superfamily, as for example MP52 (DE 195 25 416.3), were also proven to be active.

This activity of MP121 can be useful for the treatment of diseases at the eye as for example the retina or the optic nerve. It is especially useful for injuries of the neural retina and the optic nerve. Such injures can be evoked for example by accidents, inflammations or disturbance of the supply of blood. It can also be useful for the transplantation of the retina. Furthermore the treatment of other cerebral nerves is important. One example is the trigeminal nerve (Nervus Trigeminus), which also provides parts of the eye. Therefore, members of the TGF-β family, especially MP52 and MP121, can also be useful for the transplantation of the cornea. Additionally the treatment of partial damage of the cornea as for example evoked by a herpes infection can be possible. Furthermore the treatment of degenerative disorders at the surface of the eye are of interest.

Figure 8:
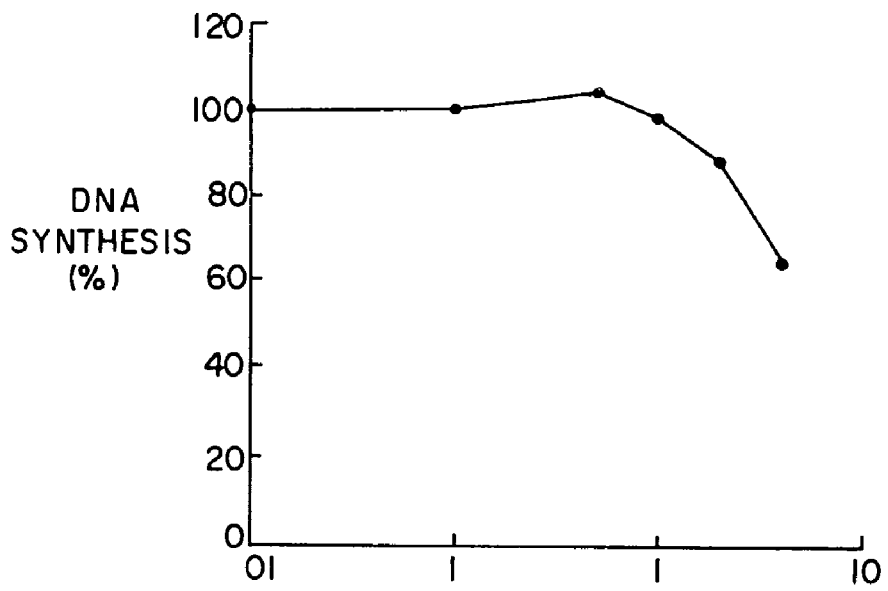
FIG. 8 shows that various concentrations of partially purified MP121 can inhibit EGF induced DNA synthesis in hepatocytes.

Results on rat hepatocyles in primary cultures indicate that partial purified MP121 inhibits the initiation of DNA synthesis (FIG. 8). The effect of MP121 resembles that of Activin A and TCF-β (Yasuda et al., J. Clin. Invest. Vol. 92, 1491–1496 (1993)) but the concentrations of MP121 which are necessary to block the growth promoting actions of EGF are higher. Nevertheless it can be assumed that MP121 can influence liver growth. Therefore it can be useful in several liver diseases including liver carcinomas.

Activin A is furthermore known for its ability to promote the differentiation of Friend erythroleukemic cells (F5-5) wherefore it was also designated Erythroid differentiation factor (EDF) (Eto et al., Biochem. Biophys. Res. Com. 142, 1095–1103 (1987)). Partial purified MP121 shows also a slight activity in this assay system. Therefore MP121 can be useful in stimulation of erythropoiesis.

The present invention in addition concerns a process for the production of a protein of the TGF-β family which is characterized in that a host cell transformed with a DNA according to the invention or with a vector according to the invention is cultured and the TGF-β protein is isolated from the cell or/and the culture supernatant. Such a process comprises culturing the transformed host cell in a suitable culture medium and purifying the TGF-β-like protein formed. In this way the process enables the production of an adequate amount of the desired protein for use in medical treatment or in applications using cell culture techniques in which growth factors are needed. The host cell can be a bacterium such as Bacillus or E. coli, a fungi such as yeast, a plant cell such as tobacco, potato or arabidopsis or an animal cell, especially a vertebrate animal cell line such as Mo, Cos or CHO cell lines or an insect cell line. Using the Baculovirus system, expression can also be performed in insect larvae. When producing in bacteria it is possible that the protein according to the invention is produced in the form of inclusion bodies. These inclusion bodies are then renatured according to known methods and the protein is then obtained in an active form (see e.g., Jaenicke, R, and Rudolph, R., Protein Structure, ed. Creighton, T. E., IRL Press, chapter 9). For the production of heterodimeric proteins with other members of the TGF-β family, both protein monomers are expressed either in the same cell or separate in the course of which a common renaturation seems suitable with formation of inclusion bodies. Viral systems such as e.g. the Baculovirus system or the Vaccinia virus system as in particular suitable when coexpressing in the same cell. The production of heterodimeric proteins is in principle known to a person skilled in the art and is described for example in WO93/09229 and EP 0 626 451 A2.

The production of chimeric proteins containing other protein parts requires a corresponding change at the DNA level which is familiar to a person skilled in the art and can be carried out by him (EMBO J. 10 (1991), 2105–2110, Cell 69 (1992), 329–341; J. Neurosci. 39 (1994), 195–210).

Yet another subject matter of the present invention is the provision of pharmaceutical compositions which contain a pharmaceutically effective amount of a TGF-β-like protein according to the invention as the active substance. If desired, such a composition comprises a pharmaceutically acceptable carrier or auxiliary substance, diluent or filling agent. Such a pharmaceutical composition can be used alone or in combination with other active substances for example other proteins of the TGF-β family or growth factors such as EGF (epidermal growth factor) or PDGF (platelet derived growth factor) in wound healing and tissue regeneration. Furthermore such a pharmaceutical composition can be used for the prevention of diseases.

Further subject matters are pharmaceutical compositions which contain heterodimeric proteins or/and chimeric proteins according to the invention.

The pharmaceutical composition according to the invention is preferably used for the treatment and prevention of damage to bones, cartilage, liver, connective tissue, skin, mucous membranes, endothelium, epithelium, neurones, kidneys or teeth, for application in dental implants, for application in wound healing or tissues regeneration processes, induction of the proliferation of precursor cells or bone narrow cells, for the maintenance of a state of differentiation and for the treatment of disturbances in fertility or for contraception.

Furthermore the pharmaceutical composition according to the invention can be useful for the treatment of diseases concerning the metabolism, such as digestive disorders or disorders concerning the level of bloodsugar.

A further possible clinical application of the TGF-β-like protein according to the invention is the use as a suppressor of immunoreactions in order to avoid rejection of organ transplants or use in connection with angiogenesis.

Furthermore the protein according to the invention can be used to increase fertility or in contraception. The pharmaceutical composition according to the invention can also be used prophylactically or in cosmetic surgery. Furthermore the application of the composition is not limited to humans but can also include animals in particular pets and domestic animals.

Thus the part of the other protein or other monomer can be used to vary the scope of applications and specificity of heterodimeric proteins and chimeric proteins as desired.

In general diseases which are associated with the expression of MP121 can be treated using the proteins according to the invention either by increasing the amount or activity of MP121 which is present or by suppressing the MP121 activity. Thus the invention also concerns the production of antisense nucleic acids and ribozymes which inhibit the translation of MP121. This inhibition can either be achieved by masking the mRNA with an antisense nucleic acid or by cleavage with a ribozyme.

The production of antisense nucleic acids is known (Weintraub, H. M., Scientific American 262: 40 (1990)). The antisense nucleic acids hybridize with the respective mRNA and form a double-stranded molecule which an then no longer be translated. The use of antisense nucleic acid is for example known from Marcus-Sekura, C. J., Anal. Biochem. 172 (1988), p. 289–295.

Ribozymes are RNA molecules which are able to specifically cleave other single-stranded RNA molecules similar to DNA restriction endonucleases. The production of ribozymes is described in Cech, J. Amera. Med. Assn. 260 (1988), p. 3030.

In this connection it is also possible according to the invention to transfect suitable vectors containing the DNA sequence according to the invention in vitro or in vivo into patient cells or to transfect the vector in vitro into cells and then to implant these in a patient.

MP121 antisense polynucleoitdes can also be introduced into cells which exhibit an undesired expression of MP121.

The MP121 activity can also be suppressed by binding molecules to the MP121 receptors which, in contrast to MP121, do not trigger further transmission of a signal.

Thus within the scope of the invention the receptors for MP121 on cells are also of interest. In order to find receptors, firstly various cell lines can be tested for their binding properties with respect to radioactivity labelled MP121 ($^{125}$I-MP121) with subsequent cross-linking. A cDNA library can subsequently be established in an expression vector (obtainable from InVitrogen) from cells which bind MP121. Cells which have been transfected with receptor cDNA can then be selected by the binding of radioactively labelled MP121. These are methods known to a person skilled in the art and have for example been used to isolate activin (Mathews, L. S. & Valve, W. W., Cell 65 (1991), 973–982) and TGF-β type II receptors (Lin. H. Y. et al., Cell 68 (1992), 775–785). In analogy to known activin receptors, the MP121 receptor is also presumably a receptor complex which belongs to this family so that further methods known to a person skilled in the art, such as e.g. PRC with degenerate oligonucleotides, can be used to find parts of the heteromeric complex. This method has also been used for example with the activin and the TGF-β type I receptors (Tsuchida et al., Proc. Natl. Acad. Sci. USA 90 (1993), 11242–11246; Attisano et al., Cell 75 (1993), 671–680; Franzén et al., Cell 75 (1993), 681–692).

Finally the present invention concerns an antibody which can bind specifically to the proteins according to the invention or such an antibody fragment (e.g. Fab or Fab'). Processes for the production of such a specific antibody or antibody fragment are part of the general knowledge of an average person skilled in the art. Such an antibody is preferably a monoclonal antibody. Such antibodies or antibody fragments can also be suitable for diagnostic methods.

In addition it is intended to illustrate the invention by the following examples.

EXAMPLE 1

Isolation of MP121

1.1 Total RNA was isolated from human liver tissue (40 year old man) according to the method of Chirgwin et al. (Biochemistry, 18, 5294–5299 (1979)). Poly (A+)-RNA was separated from the total RNA by oligo (dT) chromatography according to the manufacturer's instructions (Stratagene poly (A) Quick columns).

1.2 For the reverse transcription reaction 1 to 2.5 µg poly (A+) RNA was heated for 5 minutes to 65° C. and quickly cooled on ice. The reaction mixture contained 27 U RNA-Guard (Pharmacia), 2.5 µg oligo $(dT)_{32-18}$ (Pharmacia), 5×buffer (250 mmol/l Tris/HCl pH 8.5, 50 mmol/l $MgCl_2$, 50 mmol/l DTT, 5 mmol/l of each dNTP, 600 mmol/l KCl) and 20 U AMV reverse transcriptase (Boehringer Mannheim) per µg poly (A+) RNA. The reaction mixture (25 µl) was incubated for 2 hours at 42° C. The cDNA pool was stored at −20° C.

1.3 The deoxynucleotide primers OD and OID shown in FIG. 2 were prepared on an automatic DNA synthesizer (Biosearch). Purification was carried out by means of denaturing polyacrylamide gel electrophoresis and isolating the main bands from the gel by isotachophoresis. The oligonucleotides were designed by comparing nucleic acid sequences of known members of the TGF-β family and selecting regions with high conservation. A comparison of this region is shown in FIG.

2. In order to facilitate cloning, both oligonucleotides contained Eco RI cleavage sites and OD additionally contained a Nco I restriction cleavage site at its 5' terminus.

1.4 In the PCR reaction cDNA corresponding to 20 ng poly (A+) RNA were used as starting material (see 1.2) The reaction was carried out in a volume of 50 µl and contained 1×PCR buffer (16.6 mmol/l $(NH_4)_2SO_4$, 67 mmol/l Tris/HCl pH 8.8, 2 mmol/l $MgCl_2$, 6.7 µmol/l EDTA, 10 mmol/l β-mercaptoethanol, 170 µg/ml bovine serum albumin (Gibco), 200 µmol/l of each dNTP (Pharmacia), 30 pmol of each oligonucleotide (OD and OID) and 1.5 U Taq polymerase (AmpliTaq, Perkin Elmer Cetus). The reaction mixture was overlayed with paraffin and 40 PCR cycles were carried out. The products of the PCR reaction were purified by means of phenol/chloroform extraction and concentrated by ethanol precipitation.

1.5 Half of the PCR reaction products was cleaved with the restriction enzymes SphI (Pharmacia) and AlwNI (Biolabs) according to the manufacturer's instructions. The other half was cleaved in a series of reactions using Ava 1 (BRL), AlwN I (Biolabs) and Tfl T (Biolabs). The restrictions were carried out in 100 µl using a U enzyme for 2 to 12 hours at 37° C. (apart from Tfi I at 65° C.).

1.6 The products of the restriction cleavage were fractionated by means of agarose gel electrophoresis. After staining with ethidium bromide, uncleaved amplification products were cut out of the gel and isolated by phenol extraction. The DNA obtained was subsequently purified twice by phenol/chloroform extraction.

1.7 A quarter or a fifth of the isolated DNA was reamplified after ethanol precipitation using the same conditions as for the primary amplification except that the number of cycles was reduced to 13. The reamplification products were purified, cleaved with the same enzymes as above and uncleaved produces were isolated from the agarose gels as elucidated above for the amplification products. The reamplification step was repeated.

1.8 After the last isolation from the gel, the amplification products were cleaved by 4 U Eco RI (Pharmacia) under the conditions recommended by the manufacturer. A quarter of the restriction mixture was ligated into the vector pBluescript SK+ (Stratagene) which had been cleaved with Eco RI. After ligation, 24 clones of each enzyme combination were analyzed further by sequencing. There were no new sequences in the mixture which had been cleaved with AlwN I and Sph I, it contained only BMP6 and inhibin βA sequences. 19 identical new sequences, named MP121, were found in the mixtures cleaved with Ava I, AlwN I and Afi T. These plasmids were named pSK-MP121(OD/OID). One sequence differed by two nucleotides from this sequence that was otherwise found. Ligation and transformation in E. coli was carried out as described in Sambrook et al., Molecular Cloning; A Laboratory Manual (1989).

The clone was extended to the 3' end of the cDNA according to the method described in detail by Frohmann (published by Perkin-Elmer Corp., Amplifications, 5, 11–15 (1990)). The same liver mRNA which had been used to isolate the first MP121 fragment was reversely transcribed as described above using oligo dT (16mer) linked to the adapter primer (AGAATTCGCATGCCATGGTCGAC-GAAGC-$T_{16}$) (SEQ ID NO:33) The amplification was carried out using the adapter primer (AGAATTCGCATGC-CATGGTCGACG) (SEQ ID NO:34) and an internal primer (GGCTACGCCATGAACTTCTGCATA) (SEQ ID NO:35) prepared from the MP121 sequence. The amplification products were prepared using a further internal primer (ACAT-AGCAGGCATGCCTGGTATTG) (SEQ ID NO:36) prepared from the MP121 sequence and with the adapter primer. After restriction with Sph I the reamplification products were cloned into the vector pT7/T3 U19 (Pharmacia) which had been cleaved in the same way and sequenced. The clones were characterized by their sequence overlap with the already known part of the MP121 sequence. One clone, named p121Lt 3'MP13, was used to isolated a Nco I (made blunt using T4 polymerase)/Sp I fragment. This fragment was cloned into one of the above-mentioned pSK-MP121 (OD/OID) vectors whose OD primer sequence was orientated towards the T7 primer of the pSK multiple cloning site. For this the vector was cleaved with Sph I and Sma I. The construct was named pMP121DFus6. It comprises the MP121 sequence from position 922 to 1630 as shown in SEQ ID NO:1.

1.9 A Dde I fragment of pMP121DFus6, which extends from position 931 to 1304 in SEQ ID NO:1, was used to screen a human liver cDNA library (Clontech, #HL3006b, lot 36223) as described in detail by Ausubel et al., (Current Protocols in Molecular Biology published by Greene Publishing Associates and Wiley-Interscience (1989)). Twenty-four mixed plaques were picked from $8.1 \times 10^5$ phages and separated. From this, 10 cones which yielded a positive signal using primer LO2 (ACATAGCAGGCATGCCTGG-TATTG) (SEQ ID NO:36) and LOI1 (CTGCAGCTGTGT-TGGCCTTGAGA) (SEQ ID NO:37) from the Dde I fragment were selected and separated. The cDNA was isolated from the phases by means of an EcoRI restriction and cloned into the pBluescript SK vector which had also been cleaved with EcoRI.

Sequencing of one of the resulting plasmids SK121L9.1 showed that the start codon begins at position 128 of SEQ ID NO. 1 since three stop codons are positioned in-frame in front of this start codon at positions 62, 77 and 92. Mature MP121 starts at position 836 of SEQ ID NO. 1 assuming sequence analogy to other TGF-β proteins which corresponds to amino acid 237 in SEQ ID NO. 2. The stop codon begins at position 1184 of SEQ ID NO. 1.

Plasmid SK121L9.1 was deposited at the DSM on the 26.04.1994 under the deposit number 9177.

1.10 Isolation of the MP121 cDNA and genomic DNA from the mouse: The sequence information from the human MP121 sequence was used to isolate the MP121 sequence from the mouse. The methods used for this are all known to a person skilled in the art and are described, for example, in Current Protocols in Molecular Biology (Ausubel et al., Greene Publishing Associates and Wiley-Interscience, Wiley & Sons, 1987–1995) or in Molecular Cloning (Sambrook et al., second edition, Cold Spring Harbour Laboratory Press, 1989). Firstly, the primers ACGAATTCCGAC-GAGGCATCGACTGC (SEQ ID NO:38) and GCGTCGACTACCATGTCAGGTATGTC (SEQ ID NO:39) derived from the human MP121 sequence containing additional restriction cleavage sites at the 5' end (EcoRI or SalI) were synthesized. These primers were used for amplification on genomic mouse DNA. The 0.35 kb fragment which results was subcloned in the Bluescript vector (Stratagene) and used as a radioactive probe. A λ bank with genomic mouse DNA as well as a bank with cDNA was screened according to standard methods. The cDNA was synthesized from RNA, which had been isolated from mouse liver and cloned into λgt10 using EoRI/NotI linkers.

MP121 clones were isolated from the genomic as well as from the cDNA bank. A cDNA containing the complete coding sequence was subcloned into the EcoRI cleavage site of the Bluescript vector SK (Stratagene) and the resulting plasmid SKMP121 mouse was deposited on 10.05. 1995 at the DSM (DSM 9964). Complete sequencing resulted in the sequence shown in SEQ ID NO:3. The start codon begins at position 131 in SEQ ID NO:3 and ends at the stop codon starting at position 1187. The protein derived from the sequence is shown in SEQ ID NO:4. Subcloning and analyzing clones containing MP121 from the genomic bank showed that the MP121 sequence contains an intron in the propeptide part of ca. 5.5 kb. This intron is located between positions 446 and 447 in SEQ ID NO:3. The exon/intron junctions are shown in SEQ ID NOS:5 and 6.

EXAMPLE 2

Expression of MP121

It is possible to express MP121 in eukaryotic as well as in prokaryotic systems.

Only the mature part of MP121 was used for expression in prokaryotes. After purification the mature MP121 protein expressed in *E. coli* as a monomer can then be folded back to form a dimer. In order to simplify purification of MP121, an additional 6 histidines can be attached to the N-terminus of the mature protein which facilitate purification of the protein by binding to nickel-chelate columns.

As an example, the mature part of human MP121 (amino acid 237 and 352 in SEQ ID NO:2) with an additional 13 amino acids, including six histidines at the N-terminus, (MHHHHHHKLEFAM) (SEQ ID NO:40) was expressed in the prokaryotic vector pBP4. This vector is a pBR322 derivative having tetracycline resistance which, in addition, contains the T7 promoter from the pBluescript II SK plasmid (Stratagene). Furthermore, the vector contains a ribosomal binding site following the T7 promoter and a start codon followed by six codons for histidine. A terminator (Tφ) follows after several single restriction cleavage sites such as EcoRI, XhoI, SmaI and ApaI, for the insertion of inserts as well as stop codons in all three reading frames. In order to obtain the cDNA for the mature part of MP121, PCR was carried out on the plasmid SK121L9.1 (DSM depository number: 9177) using the two oligonuleotides GAATTCGC-CATGGGCATCGACTGCCAAGGAGG (SEQ ID NO:4) and CCGCTCGAGAAGCTTCAACTGCACCCACAGGC (SEQ ID NO:42). Both oligonucleotides contain addition al restriction cleave sites at their ends (EcoRI and NcoI or XhoI and HindIII). In an intermediate step of the resulting 377 bp fragment was cloned with blunt ends into the pBluescript II SK vector (Stratagene) that had been cleaved with EcoRV. One clone in the orientation of the 5' end of MP121 towards the T7 promoter was cleaved with EcoRI and the resulting insert (0.38 kb) was cloned into the pBP4 vector that had also been cleaved with EcoRI. The correct orientation of the insert in the resulting plasmid pBP4MP121His was established by restriction analysis and sequencing. The plasmid pBR4MP121His was deposited on 30.1.1995 at the DSM (depository number: 9704). The expression of MP121 protein can be achieved by simultaneously providing T7 RNA polymerase. T7 RNA polymerase can be provided by various methods such as, e.g., by a second plasmid with a gene for T7 RNA polymerase or by infection with phages which code for T7 RNA polymerase or also by special bacterial strains which have integrated the gene for T7 RNA polymerase. The mature MP121 protein with a His-tag (MP121His) is produced in inclusion bodies by using the bacterial strain BL21 (DE3)pLysS (Novagen, #69451-1) and inducing the T7 RNA polymerase expression with IPTG according to the manufacturer's instructions. In SDS polyacrylamide gels (15%) the protein exhibits an apparent molecular weight of nearly 16 kD (theoretical molecular weight: 14.2 kD) as is shown representatively in the Western blot of FIG. 3. The bacteria transformed with pBP4 as controls do not show any staining of specific bands. Due to the His-tag this protein can be purified on nickel-chelating agent columns as described, for example, by Hochuli et al., (Bio/Technology, Vol. 6, 1321–1325 (1988)). An additional purification is possible by means of reversed phase HPLC. A reversed phase column (Nucleosil 300-7C4 from Macherey-Nagel, Type 715023) was used with a flow-rate of 2 ml/min and an acetonitrile gradient in 0.1% TFA of 0 to 90% within 100 minutes. MP121 His elutes under these conditions after ca. 40% acetonitrile.

The mature part of MP121 (amino acid 237 to 352 in SEQ ID NO.2) was additionally expressed in *E. coli* with one additional methionine at the N-terminus only using again a system with the T7 RNA Polymerase. The expression level was improved by including a gene for the lacI repressor in the expression plasmid (as it is used in the pET vectors from Novagen) and using another *E.coli* strain, HMS 174(DE3) (Novagen #69453). Inclusion bodies can be isolated by standard methods and washed with 2 M guanidinium chloride /HCL in 20 mM Tris pH 8.0. MP121 is further purified by a reversed phase HPLC as described for MP121His.

Additionally, monoclonal antibodies were developed in mice. A peptide of 26 amino acids from the mature part of MP121 was used as an antigen: PLSLLYYDRDSNIVKT-DIPDMVVEAC (SEQ ID NO:43). The antigen was coupled to ovalbumin using the free SH group of the cysteine according to conventional methods. Other constructs could be used as antigens also, as for example, the dimeric mature MP121.

Immunization of BALB/c mice was performed according to conventional methods. The coupled peptide was used for example as antigen in combination with complete Freund's adjuvant for the first immunization and in combination with incomplete Freund's adjuvant in successive immunizations. The antigen (5–10 µg each time) was injected subcutaneously in the hind limbs of three mice at day 17, 14, 10, 7, 4 and 1 before the isolation of popliteal lymphatic nods underneath the knee joint. A suspension of cells was produced for fusion to myeloma cells (P3×63Ay8.653, ATCC, CRL 3580) by the help of PEG. These techniques are described in more detail by Peters, J. H. & Baumgarten, H. (1990, Monoklonale Antikörper—Herstellung und Charakterisierung, Springer Verlag, 2.Auglage). It is possible to select for fused hybridomas by addition of azaserina and hypoxanthine. The supernatants of different walls were tested after 8–10 days with ELISA and Western blot analyses using MP121 expressed in eukaryotic and prokaryotic cells. The cells with the best positive results were further subcloned to isolate cells producing only one monoclonal antibody. To purify the monoclonal antibodies 1 liter of cell culture supernatant containing the monoclonal antibody was produced using roller bottles (Schott) in a "Cell-Roll" (Former Scientific) according to standard methods. The antibodies of the cell culture supernatants can be concentrated and subsequently purified using a protein G column (ImmunoPure Pluse (G) IgG Purification Kit, Piece, #44795) according to the manufacturer's instructions. The monoclonal antibodies derived by this method proved to be useful for the detection of MP121.

In each case the determination whether it is MP121 protein was carried out by means of Western blot analysis using MP121-specific antibodies. Polyclonal antibodies against MP121 were produced in chicken as well as in rabbits. In order to obtain the antigen for the immunization, a part of the mature part of MP121 (amino acid 260 to 352 in SEQ ID NO.2) was fused with the first 98 amino acids of the polymerase of the MS2 bacteriophage and expressed in E. coli. After isolating the inclusion bodies, the fusion protein (MS2-MP121) was separated on polyacrylamide gels and isolated for the immunization after staining with copper by means of electro-elution (Tessmer, U. & Dernick, R., IBL (1990) 8–13). It is possible to specifically detect the expression of MP121 using antibodies from chicken as well as from rabbits. Chicken antibodies were used for the schematic Western blot in FIG. 1 which had been purified further by means of PEG precipitation (Thalley B. S. and Carroll, S. B. BIO/Technology Vol. 8, 934–938 (1990)) and by means of membrane-bound antigen (fusion protein (MS2-MP121)) (18.17 in Sambrook et al., Molecular Cloning, second edition, Cold Spring Harbor Laboratory Press 1989). Anti-chicken IgG coupled to alkaline phosphatase (Sigma A9171) was used as the second antibody. The detection was carried out according to the manufacturer's instructions using the Tropix Western-Light Protein Detection Kit (Serva #WL10RC).

In order to obtain biologically active material, the purified monomeric MP121 expressed in E. coli can be folded back to form a dimeric MP121. This can be carried out according to the methods for example described by Jaenicke, R. & Rudolph, R. (Protein structure, ed. Creighton, T. E., IRL Press, chapter 9).

The Vaccinia virus expression system was used for expression in eukaryotic cells as it is described in detail and in a form which can easily be repeated by a person skilled in the art in Current Protocols in Molecular Biology (Ausubel et al., Greene Publishing Associates and Wiley-Interscience, Wily & Sons) abbreviated in the following as CP, in chapter 16 unit 16.15–16.18. The system is based on the fact that foreign DNA can be integrated by homologous recombination into the genome of the Vaccinia virus using certain vectors. For this purpose the vector used contains the TK (thymidine kinase) gene from the Vaccinia genome. In order to enable selection for recombinant viruses, the vector additionally contains the E. coli xanthine-guanine-phosphoribosyl transferase gene (gpt) (Falkner, F. G. & Moss, B., J. of Virol. 62 (1988), 1849–1854). The cDNA with the complete region coding for MP121 was cloned into this vector.

PCR reactions and intermediate cloning were necessary in order to shorten the 5' and 3' untranslated regions of the initial plasmid SK121L9.1 (DSM, depositary number; 9177) and to insert single restriction cleavage sites at the ends. All PCR reactions were carried out using the plasmid SK121L9.1 (DSM depositary number:9177). In order to shorten the 5' untranslated end, the primer CCCGGATC-CGCTAGCACCATGACCTCCTCATTGCTTCTG (SEQ ID NO:44) with an inserted BamHI and NheI restriction cleavage site was used in a PCR with an internal primer (CCCTGTTGTCCTCTAGAAGTG) (SEQ ID NO:45). In an intermediate step, the fragment obtained was cloned into Bluescript SK (Stratagene), sequenced and checked for concurrence with the sequence shown in SEQ ID NO:1. The SphI/EcoRI fragment (0.22 kg) from the plasmid pBP4MP121His was used to shorten the 3' untranslated end. Both end fragments of MP121 were linked to the missing middle DNA sequence from the plasmid SK121L9.1 (DSM depositary number: 9177) by means of internal restriction cleavage sites (Xba I and Sph T) according to standard methods (Sambrook et al. Molecular Cloning, second edition, Cold Spring Harbor Laboratory Press 1989). The shortened cDNA obtained in this way having the complete reading frame for MP121 (nucleotide 128 to nucleotide 1184 in SEQ ID NO:1) could be cloned into the vector pBP1 which had also been cleaved by using the restriction cuts Bam HI and Eco RI. The resulting plasmid pBP1MP121 was deposited on 12.1.95 at the DSM (depositary number: 9665).

The plasmid pBP1MP121 was used for the production of recombinant Vaccinia viruses. For this 143B cells (HuTk-, ATCC CRL 8303) which were 80% confluent were infected with Vaccinia wild-type virus (1 virus per 10 cells) in 1 ml PBS in 35 mm culture plates for 30 minutes at room temperature while shaking occasionally. After aspirating the supernatant and adding 2 ml culture medium (MEM, Gibco BRL #041-01095 containing 1:500 diluted penicillin and streptomycin Gibco BRL #043-01540), they were incubated for 2 hours at 37° C. Subsequently the medium was removed and these cells were transformed for ca. 15 hours at 37° C. using 100 ng pBP1MP121, 2 µg carrier DNA (calf rhymus, treated with ultrasound, Boehringer Mannheim #104175) and 10 µl Lipofectin (Gibco BRL #18292-011) in 1 ml MEM. After addition of 1 ml MEM containing 20% FCS (Sigma #F-7524) they were incubated for a further 24 hours at 37° C. and subsequently the lysed cells were frozen.

Gpt selection for xanthine-guanine-phosphoribosyl transferase and isolation and amplification of individual recombinant viruses was essentially carried out as described in unit 16.17 of CP with the difference that RK13 cells (ATCC CCL 37) were used.

Integration of the MP121 cDNA into the viral genome was confirmed by dot blot analysis (CP unit 16.18). A recombinant virus from the transfection with pBPMP121 and the wild-type virus wee used for expression analyses in cell lines 143B (HuTK-, ATCC CRL 8303, human) and NIH-3T3 (DSM ACC 59, Swiss mouse embryo). The cells were cultured according to the distributor's instructions. Confluent cells were infected for 30 minutes at 37° C. with the three-fold number of viruses and subsequently the respective culture medium containing 10% FCS and penicillin/streptomycin (1:500, Gibco BRL #043-05140) was added. The medium was removed after 6 hours at 37° C., the cells were washed twice with e.g. HBSS (Gibco BRL #14180-046) and production medium (MEM for HuTk- or DMEM containing 4.5 g/l glucose and NEAA (Gibco BRL #11140-035) for HIN-3T3 each of which contained aprotinin (Fluka #10820, 50 U/ml) and penicillin/streptomycin) without FCS. After a production period of 20 to 22 hours, the cell supernatant was collected. The expression was analysed by means of Western blots according to standard methods (CP unit 10.8). For this the proteins from 1 to 3 ml cell culture supernatant were precipitated by addition of an equivalent volume of acetone and incubating for at least one hour one ice and centrifuged. After resuspending the pellets in application buffer (7 M urea, 1% SDS, 7 mM sodium dihydrogen phosphate, 0.01% bromophenol blue and 1β-mercaptoethanol if desired) they were separated in 15% polyacrylamide gels. A pre-stained protein molecular weight standard (Gibco BRL #6041-020) was used as marker proteins. Transfer onto a PVDF membrane (Immobilon #IPVH00010) and blocking the membrane was carried out according to standard methods.

A representative schematic diagram of the results of the Western blot in FIG. 3 shows that MP121-specific bands occur in the recombinant virus infected cells. The expression of MP121 in NIH-3T3 cells leads to a secreted protein with an apparent molecular weight in the gel of about 18 kD under non-reducing conditions (expected theoretical molecular weight: 25 kD). Under reducing conditions the protein migrates at about 15 kD in the gel (expected theoretical molecular weight: 12.5 kD). These results show that MP121 is expressed as a dimeric mature protein as expected. The migration behaviour of the dimeric MP121 protein which is only slightly slower than the monomeric MP123 protein is probably due to its globular structure. The processing of the precursor protein to form the mature protein could also be demonstrated in HuTk cells. No bands occurred in the Western blot with cells (HuTk- or NIH-3T3) infected with wild-type viruses (without integrated foreign DNA).

Figure 6:
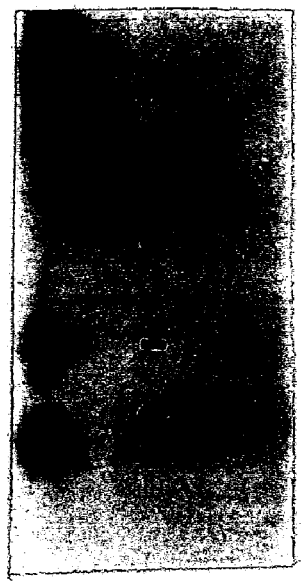
FIG. 6 shows a Western blot using rabbit antibodies against human MP121. Lane 1 shows cell culture supernatant of HepG2 cells after infection with recombinant viruses (with inserted MP121 cDNA) under non-reducing conditions. Lane 2 shows cell culture supernatant of HepG2 cells after infection with wildtype viruses under non-reducing conditions. Lane 3 shows prestained protein molecular weight markers having apparent molecular weights of 15.5, 18.2, 27.8, 43.8 and 71.5 kD (Gibco BRL #26041-020), indicated schematically. Lane 4 shows cell culture supernatant of HepG2 cells after infection with recombinant viruses (with inserted MP121 cDNA) under reducing conditions. Lane 5 shows cell culture supernatant of HepG2 cells after infection with wildtype viruses under reducing conditions.

Further expression studies of MP121 using the Vaccinia virus system revealed that several cell lines express in addition to the dimeric MP121 also significant amounts of a monomeric form. This monomeric form seems to be folded and has a more globular structure because it runs faster in PAGE/Western blot analyses than the reduced monomer derived from the dimeric MP121 after treatment with DTT. FIG. 6 shows the expression of dimeric and monomeric MP121 in HepG2 cells (Heptocellular carcinoma, human, ATCC HB 8065). A residual unprocessed precursor form appears in addition. It was already shown by our Northern blot analysis that the HepG2 cells naturally transcribe the MP121 gene, therefore it can be assumed that the appearance of monomeric MP121 is of physiological relevance.

The monomeric MP121 was found besides the dimeric MP121 in significant amounts in MvlLu (NBL-7, lung, mink, ATCC CCL64) and Hela (Epitheloid carcinoma, cervix, human, ATCC CCL2) too. In addition, MP121 was expressed using the Baculovirus expression system (Invitrogen). After infection of insect larvae (Trichoplusia ni) with recombinant viruses, MP121 was detected in the haemolymph after 3–4 days in the dimeric form.

When co-transfection with recombinant Vaccinia viruses that code for various members of the TGF-β family has also taken place, the Vaccinia virus expression system is also particularly suitable for the production of heterodimers. It is then possible to separate heterodimers from homodimers by affinity columns using specific antibodies against the individual members of the TGF-β family. In this case the α a well as βA and βB chains of inhibins are of particular interest.

EXAMPLE 3

Investigation of the expression of MP121 in various mouse tissues

Total RNA from various tissues (brain, heart, kidney, liver, lung, spleen, muscle, ovary, testes) was isolated according to standard methods from six-week-old mice as well as from embryonic stem cells. 10 µg total RNA was used in each case in a RNAase protection assay (RPA) from Ambion (RPA II kit, #1410) according to the manufacturer's instructions. In order to obtain specific probes for activin $\beta_A$ and activin $\beta_B$ the genomic DNA from mouse (129Sv) was amplified from the mature part of the proteins using corresponding specific primers. In order to facilitate cloning, EcoRI and/or BamHI or HindIII restriction cleavage sites were introduced, respectively, at the ends of the primers. In the case of activin $\beta_A$ the primers were derived from mRNA from rats (GenBank Accession #M37482):

GGATCCGAATTCGGCTTGGAGTGTGATG-GCAAGG (SEQ ID NO:46) and GGATCCGAATTC-CTCTGGGACCTGGCAACTCTAG (SEQ ID NO:47).

The resulting PCR fragments were subcloned into the vector pGEM-4 (Promgea) and tested. The activin-specific and thus in the RPA protected sequences have a fragment size of 369 bp in the case of activin $\beta_A$ and 254 bp in the case of activin $\beta_B$. In MP121 the protected fragment comprises the sequence from position 887 to position 1164 in SEQ ID NO.3. The fragments cloned into pGEM-4 were transcribed in vitro in order to produce radioactively labelled antisense RNA probes. This was carried out according to the manufacturer's instructions (Promega, Riboprobe Gemini Systems) using 100 µM CTP and at the same time $\alpha^{32}$P-CTP (800 Ci/mmol, Amersham). A radioactively labelled RNA was also synthesized as a control from the plasmid pTri-GAPDH (Ambion #7431) linearized with Dde I but using 1 mM CTP. After isolating the 4 antisense RNA probes from polyacrylamide gels, these were incubated at 42° C. overnight in the same mixture with the respective tissue RNA from the mouse (10 µg total RNA per probe having $1\times10^5$ cpm). It was analyzed in a denaturing gel according to standard methods with a subsequent autoradiography for 4 days.

The analysis of MP121 mRNA expression in liver cells or remnant liver was performed likewise or using Northern blot analysis according to standard procedures (see CP, Chapter 4 or Molecular Cloning, Sambrook et al., 2nd Edition, Cold Spring Harbor Laboratory Press 1989).

Hepatocytes were isolated from rat (Wistar) liver and cultured according to Yasuda et al. (J. Clin. Invest. Vol. 92, 1491–1496 (1993)). The cells were washed prior to incubation with fresh serum-free medium containing 0.1 nM insulin, 0.1% BSA, optionally 1 nM EGF and (1 nM) partially purified MP121 (see Example 4).

Partial hepatectomy (about 70% of the rat liver) was performed as described by Higgins & Anderson (Arch. Pathol. 12, 186–202 (1931)) under ether anesthesia.

EXAMPLE 4

Partial Purification of MP121 and Examination of the Activity of Partially Purified MP121

The MP121 protein which had been obtained by expression in the Vaccinia virus system (see example 2) could be partially purified by means of two columns.

In order to produce MP121 confluent NIH-3T3 cells (DSM ACC 59, Swiss mouse embryo) were infected with the same number of recombinant viruses for 30 minutes at 37° C. and subsequently the appropriate culture medium containing 10% FCS and pencillin/streptomycin was added.

After 4 hours at 37° C. the medium was removed, the cells were washed twice and production medium (see Example 2) without FCS was added. After 20 to 22 hours production, the cell supernatant was collected and centrifuged in order to remove the viruses (40000×g for 30 minutes at 4° C.) and filtered (0.1 μm pore size, Millex VV, Millipore #SLVV25L9). The control supernatant (wt) was obtained in a comparable manner after infection by wild-type Vaccinia viruses. The expression of MP121 was checked by means of Western blot analysis and estimated to be 50–100 μg/l.

The cell culture supernatant containing MP121 (1.1 l) was admixed with the protease inhibitor PMSF (1 μM), brought to a final concentration of 1 M $(NH_4)_2SO_4$, 20 mM Tris pH 8.0 and loaded onto a phenyl-Sepharose (fast flow (high sub) Pharmacia #17-0973-05) column (5 ml bed) equilibrated in buffer A (1 M $(N_4)_2SO_4$, 20 mM Tris pH 8.0). The loaded column was washed with 15 column volumes of buffer A and 10 column volumes of buffer B (20 M Tris pH 8.0) and eluted within 50 minutes (5 ml per fraction) with a linear gradient to 100% buffer C (20 mM Tris pH 8.0, 80% ethylene glycol) at a flow rate of 1 ml/min. It was possible to check that MP121 eluted between 50 and 80% ethylene glycol by means of Western blot analysis. Aliquots of these fractions wee examined using 15% polyacrylamide silver-stained gels according to the manufacturer's instructions (Silver Stain-II, Daiichi #SE140000) and the fractions containing MP121 were pooled. After purification of the control supernatant comparable fractions were also pooled after analysis in silver-stained gels.

The pooled fractions were purified further with the aid of reversed phase HPLC. For this a CB column (Aquapore RP300, Applied Biosystems, particle size; 7 μm, pore size: 300Å) was equilibrated with buffer A (0.1% trifluoroacetic acid/water). After loading the column with the pooled fractions containing MP121 from the phenyl-Sepharose column, it was extensively washed with buffer A. The bound protein was eluted at a flow rate of 0.2 ml/min using a linear gradient of 1.5% buffer B (90% acetonitrile, 0.1% trifluoroacetic acid) per minute. Fractions of 600 μl were collected and analyzed in a Western blot as well as with silver-stained gels. Under the selected conditions MP121 protein eluted after about 55% acetonitrile. The fractions containing MP121 were pooled. The same was carried out with the corresponding fractions from the purification of the control supernatant. The analysis in the silver gel showed that MP121 was still contaminated by other proteins. Further purification steps are necessary to obtain pure MP121.

Other methods known to a person skilled in the art such as gel sieve columns, ion exchange columns, affinity columns or metal chelate columns could also be used for the further purification.

It was estimated from Western blot analysis that ca. 8 μg partially purified MP121 was obtained from 1 l of cell culture supernatant. The partially purified protein was stored lyophilized at −80° C.

In order to investigate the influence of MP121 on dopaminergic neurones, neurones from the mesencephalic floor of 14 day-old rat embryos (E14) were isolated according to a method described by Shimoda et al. (Brain Res. 586, 319–331 (1992)). The cells were singled out and cultured as described by Krieglstein et al., (Neuroscience 63, 1189–1196 (1994)). The cell density on polyornithine/laminin-coated cover glasses is 200000 cells/cm². After culture for 24 hours and subsequently every three days two-thirds of the medium (500 μl) was removed and replaced by fresh medium containing the respective additives. The lyophilized MP121 partially purified by phenyl sepharose and reversed phases HPLC was dissolved in 50% acetonitrile and added to the medium. The final concentration of MP121 in the medium is 20 ng/ml (the final concentration of acetonitrile is 0.3%). A comparable amount from the control supernatant (wt) which had been purified in a comparable manner was dissolved in 50% acetonitrile and added. The medium control also contains 0.3% acetonitrile. After eight days the cultures were fixed for 10 minutes at room temperature in 4% paraformaldehyde; the cells were made permeable with acetone (10 min, −20° C.) and washed with PBS (phosphate buffered saline). After treatment with 1% $H_2O_2$ in PBS, washing and blocking with horse serum, they were stained immunocytochemically. Tyrosine hydroxylase (TH) is a limiting enzyme in the biosynthesis of dopamine and other catecholamines so that TH can be used as a marker for dopaminergic neurones in the present cultures (cells containing noradranaline were not isolated). TH was detected by a 1 hour incubation at 37° C. using a mouse-monoclonal antibody against rate TH (diluted 1,2000, Boehringer Mannheim) and subsequent detection using the Vectastair ABC kit (Vecto Labs). TH-positive cells were counted in an area of 0.12 cm². It can be seen from FIG. 5 that MP121 has a positive effect on the survival of dopaminergic neurones.

Figure 7:
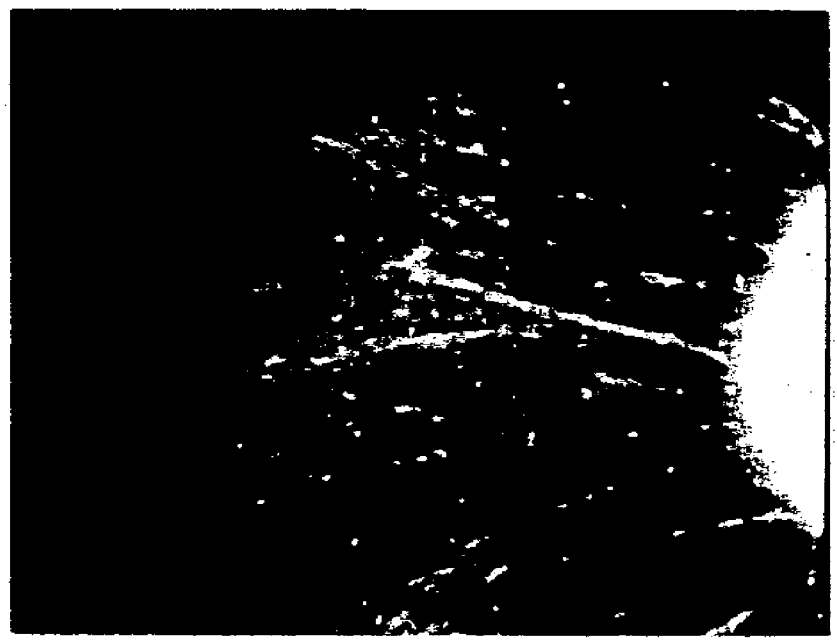
FIG. 7 shows the stimulation of nerve fibre outgrowth from the embryonic retina by treatment with partially purified MP121. Dark-field microscopy of living cultures shows nerve fibre outgrowth from explanted chicken retina after 4 days in culture in the presence of 5 ng/ml of partially purified MP121.

In order to investigate the neural influence of MP121 in another system explant cultures of the embrynoic retina were used. This organotypic culture system is described in detail by Carri, N. G. & Ebendal, T. (Dev. Brain Res. 6, 219–229 (1983)), Carri, N. G. & Edendal, T. (Anat. Rec. 214, 226–229 (1986) and Carri, N. G. et al. (J. Neurosci. Res. 19, 428–439 (1988)). This assay measures the stimulation of extending nerve fibres from the embryonic retina on a collagen substratum. Briefly, the retinal explants were taken from the chick retina (White Leghorn, embryonic day 6) and the neural retina was separated from the pigment epithelium and mesenchymal cells by repeated washing. The organotypic explants were transferred to collagen-coated culture dishes and incubated overnight (37.5° C., 5% $CO_2$). The lyophilized MP121 partially purified by Phenyl-Sepharose and reversed phase HPLC was dissolved in aqueous buffer or 50% acetonitrile and diluted in the culture medium to a final concentration of 1.25 ng/ml, 12.5 ng/ml, 25 ng/ml, 50 ng/ml, 100 ng/ml, 200 ng/ml, whereby it makes no difference in the results whether acetonitrile or aqueous buffers were used for solubilization. A comparable amount from the control supernatant (wt) which had been purified in a comparable manner was added in control assays. For the background fibre outgrowth, standard tissue culture medium with only bovine serum added was used. The incubation was continued and after a 4 day period in culture the maximum length of the leading fascicles was measured in an inverted microscope under dark-field illumination. As shown in Table 1, MP121 dose-dependently stimulated the outgrowth of nerve fibres being maximally active at about 25 ng/ml resulting in a real fibre length of about 1.7 mm. FIG. 7 shows the fibre outgrowth in a living culture after treatment with MP121 (5 ng/ml). The control (wt) did not stimulate fibre outgrowth as tested in concentrations equivalent to those used for the active MP121.

TABLE 1

Retinal neurite length after 4 days in culture treated with different concentrations of MP121. The neurite lengths of the background fibre outgrowth in the control tissue culture medium were 5.5/8/10/11/4.8/7 units giving a mean of 7.7 units (SEM 1.00). The neurite lengths of the wt control (used in equivalent concentrations as MP121) was in the same range as the background fibres. Each unit represents 0.03 mm real scale in the culture dish.

| MP121 (ng/ml) | Length (units)   | Mean ± SEM   |
|---------------|------------------|--------------|
| 1.25          | 7/12/5/6         | 7.5 ± 1.5    |
| 12.5          | 19/20/13/26      | 19.5 ± 2.6   |
| 25            | 50/52/60/71/65/53| 58.5 ± 3.4   |
| 50            | 37/32/40/41/36/20| 35.6 ± 3.8   |
| 100           | 21/8/19/18       | 16.5 ± 2.9   |
| 200           | 11/8/12/10       | 10.2 ± 0.8   |

In order to investigate the influence of MP121 on liver derived cells hepatocytes were isolated from rat (Wistar) liver and cultured according to Yasuda et al. (J. Clin. Invest. Vol. 92, 1491–1496 (1993)). The cells were washed prior to incubation with fresh serum-free medium containing 0.1 nM insulin, 0.1% BSA and 1 nM EGF. The lyophilized MP131 partially purified by phenyl sepharose and reversed phase HPLC was solubilized in acetonitrile as usually and added to the medium at various concentrations (see FIG. 8). A comparable amount from the control supernatant (wt) which had been purified in a comparable manner was us a control. The hepatocytes were incubated for 72h and 0.5 µCi [$^3$H]Thymidine/ml was included for the last 24 hours as described by Mead & Fausto (Proc.Natl. Acad.Sci.USA 86, 1558–1562 (1989)). [$^3$H]Thymidine incorporation into trichloracetic acid-precipitable material was subsequently measured an described by McNiel et al. (J. Cell. Biol. 101, 372–379 (1985)).

Figure 9:
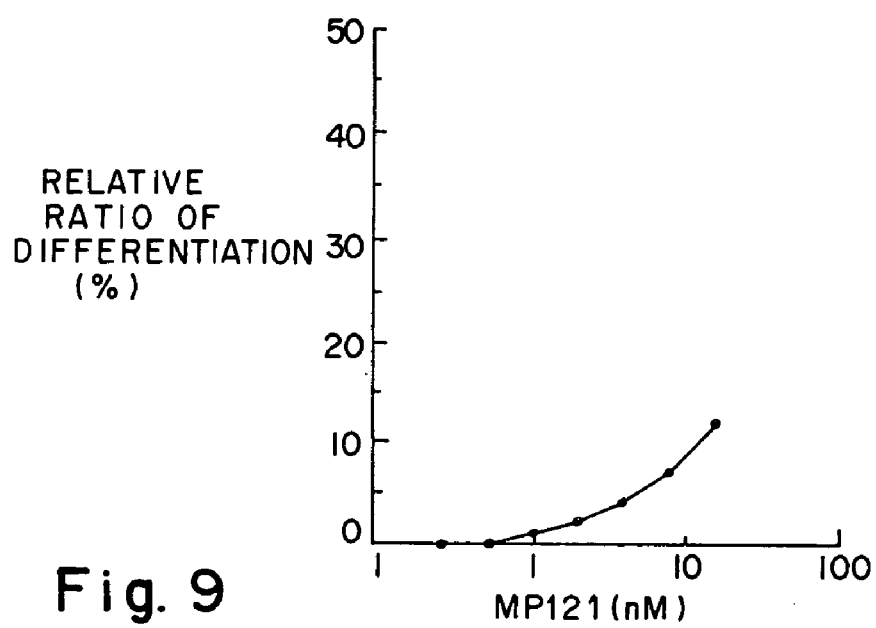
FIG. 9 shows the influence of various concentrations of partially purified MP121 on erythroid differentiation measured by the percentage of dianisidine positive cells.

In order to investigate the influence of MP121 on erythroid differentiation its influence on Friend leukemia cells (F5-5) was measured. Therefore Friend leukemia cells cultured in microtiter plates essentially as described by Eto et al. (Biochem. Biophys. Res. Com. 142, 1095–1103 (1987)). The lyophilized MP121 partially purified by phenyl sepharose and reversed phase HPLC was solubilized as already described, added to the Friend cells at various concentrations (see FIG. 9) and incubated for 5 days. The percentage of differentiated cells was determined after staining with o-dianicidine.

We claim:

1. An isolated protein of the TGF-β family which has mitogenic and/or differentiation-inductive activity and is coded by a DNA molecule selected from the group consisting of
   (a) a DNA molecule comprising the nucleotide sequence of nucleotides 866–1183 of SEQ ID NO:1;
   (b) a DNA molecule comprising the nucleotide sequence shown in the SEQ ID NO:3, or the following fragments: nucleotides 131–1186 of SEQ ID NO:3, nucleotides 839–1186 of SEQ ID NO:3, and nucleotides 869–1186 of SEQ ID NO:3;
   (c) a DNA molecule encoding the amino acid sequence encoded by (a) or (b); and
   (d) a DNA molecule comprising a nucleotide sequence (i) which hybridizes with a complement of one of the DNA molecules from (a) and (b) under stringent hybridization conditions in 6x SSC at 62–66° C. followed by one hour wash with 0.6x SSC and 0.1% SDS at 62–66° C. and (ii) which encodes a protein comprising an amino acid sequence containing seven conserved cysteine residues, said seven conserved cysteines corresponding to cystine residues at positions 247, 276, 280, 316, 317, 349 and 351 in SEQ ID NO:2.

2. A monomeric protein comprising the protein of claim 1.

3. A pharmaceutical composition comprising the protein of claim 2 and pharmaceutically acceptable carrier or auxiliary substances, diluents or fillers.

4. An isolated protein which has an amino acid sequence selected from the group consisting of SEQ ID NO:4, a mature protein that starts with one of amino acids 217–236 or 240 and ends with amino acid 352 of SEQ ID NO:2; a mature protein which comprises at least the region of seven cysteine residues, said region comprising amino acid residues 247–352 of SEQ ID NO:2, a mature protein that starts with one of amino acids 217–240 and ends with amino acid 352 of SEQ ID NO:4; and a mature protein which comprises at least the region of seven cysteine residues, said region comprising amino acid residues 247–352 of SEQ ID NO:4.

5. The protein according to claim 4, wherein said protein has an amino acid sequence selected from the group consisting of a mature protein that starts with amino acid 236 and ends with amino acid 352 of SEQ ID NO:2, a mature protein that starts with amino acid 236 and ends with amino acid 352 of SEQ ID NO:4 and a mature protein the starts with amino acid 237 and ends with amino acid 352 of SEQ ID NO:4.

6. A monomeric protein comprising the protein of claim 5.

7. A pharmaceutical composition comprising the protein of claim 6 and pharmaceutically acceptable carrier or auxiliary substances, diluents or fillers.

8. A heterodimeric protein comprising a monomer of a first protein of the TGF-β family and a monomer of another protein from the TFG-β family, said first protein has mitogenic and/or differentiation-inductive activity and is coded by a DNA molecule selected from the group consisting of
  (a) a DNA molecule comprising the nucleotide sequence shown in the SEQ ID NO:1, or the following fragments: nucleotides 128–1183 of SEQ ID NO:1, nucleotides 836–1183 of SEQ ID NO:1, and nucleotides 866–1183 of SEQ ID NO:1;
  (b) a DNA molecule comprising the nucleotide sequence shown in the SEQ ID NO:3, or the following fragments: nucleotides 131–1186 of SEQ ID NO:3, nucleotides 839–1186 of SEQ ID NO:3, and nucleotides 869–1186 of SEQ ID NO:3;
  (c) a DNA molecule encoding the amino acid sequence encoded by (a) or (b); and
  (d) a DNA molecule comprising a nucleotide sequence (i) which hybridizes with a complement of one of the DNA molecules from (a) and (b) under stringent hybridization conditions in 6x SSC at 62–66° C. followed by one hour with 0.6x SSC and 0.1% SDS at 62–66° C. and (ii) which encodes a protein comprising an amino acid sequence containing seven conserved cysteine residues, said seven conserved cysteines corresponding to cysteine residues at positions 247, 276, 280, 316, 317, 349 and 351 in SEQ ID NO:2.

9. A pharmaceutical composition comprising the protein of claim 8 and pharmaceutically acceptable carrier or auxiliary substances, diluents or filters.

10. The heterodimeric protein of claim 8 wherein the other member of the TGF-β family in activin/inhibit or a bone morphogenetic protein.

11. A pharmaceutical composition comprising a protein and pharmaceutically acceptable carrier or auxiliary substances, diluents or fillers, said protein has mitogenic and/or differentiation-inductive activity and is coded by a DNA molecule selected from the group consisting of
  (a) a DNA molecule comprising the nucleotide sequence shown in the SEQ ID NO:1, or the following fragments: nucleotides 128–1183 of SEQ ID NO:1, nucleotides 836–1183 of SEQ ID NO:1, and nucleotides 866–1183 of SEQ ID NO:1;
  (b) a DNA molecule comprising the nucleotide sequence shown in the SEQ ID NO:3, or the following fragments: nucleotides 131–1186 of SEQ ID NO:3, nucleotides 839–1186 of SEQ ID NO:3, and nucleotides 869–1186 of SEQ ID NO:3;
  (c) a DNA molecule encoding the amino acid sequence encoded by (a) or (b); and
  (d) a DNA molecule comprising a nucleotide sequence (i) which hybridizes with a complement of one of the DNA molecules from (a) and (b) under stringent hybridization conditions in 6x SSC at 62–66° C. followed by one hour wash with 0.6x SSC and 0.1% SDS at 62–66° C. and (ii) which encodes a protein comprising an amino acid sequence containing seven conserved cysteine residues, said seven conserved cysteines corresponding to cysteine residues at positions 247, 276, 280, 316, 317, 349 and 351 in SEQ ID NO:2.

12. A homodimeric protein comprising two monomers of a protein that has mitogenic and/or differentiation-inductive activity and is coded by a DNA molecule selected from the group consisting of
  (a) a DNA molecule comprising the nucleotide sequence shown in the SEQ ID NO:1, or the following fragments: nucleotides 128–1183 of SEQ ID NO:1, nucleotides 836–1183 of SEQ ID NO;1, and nucleotides 866–1183 of SEQ ID NO:1;
  (b) a DNA molecule comprising the nucleotide sequence shown in the SEQ ID NO:3, or the following fragments: nucleotides 131–1186 of SEQ ID NO:3, nucleotides 839–1186 of SEQ ID NO;3, and nucleotides 869–1186 of SEQ ID NO:3;
  (c) a DNA molecule encoding the amino acid sequence encoded by (a) or (b); and
  (d) a DNA molecule comprising a nucleotide sequence (i) which hybridizes with a complement of one of the DNA molecules from (a) and (b) under stringent hybridization conditions in 6x SSC at 62–66° C. followed by one hour wash with 0.6x SSC and 0.1% SDS at 62–66° C. and (ii) which encodes a protein comprising an amino acid sequence containing seven conserved cysteine residues, said seven conserved cysteines corresponding to cysteine residues at positions 247, 276, 280, 316, 317, 349 and 351 in SEQ ID NO:2.

13. A pharmaceutical composition comprising the protein of claim 12 and pharmaceutically acceptable carrier or auxiliary substances, diluents or fillers.

14. A pharmaceutical composition comprising a protein and pharmaceutically acceptable carrier or auxiliary substances, diluents or fillers, said protein has an amino acid sequence selected from the group consisting of a mature protein that starts with amino acid 236 and ends with amino acid 352 of SEQ ID NO:2, a mature protein that starts with amino acid 237 and ends with amino acid 352 of SEQ ID NO:2, a mature protein that starts with amino acid 236 and ends with amino acid 352 of SEQ ID NO:4 and a mature protein that starts with amino acid 237 and ends with amino acid 352 of SEQ ID NO:4.

15. A heterodimeric protein comprising a monomer of a first protein of the TGF-β family and a monomer of another protein from the TGF-β family, said first protein has an amino acid sequence selected from the group consisting of a mature protein that starts with amino acid 236 and ends with amino acid 352 of SEQ ID NO:2, a mature protein that starts with amino acid 237 and ends with amino acid 352 of SEQ ID NO:2, a mature protein that starts with amino acid 236 and ends with amino acid 352 of SEQ ID NO:4 and mature protein that starts with amino acid 237 and ends with amino acid 352 of SEQ ID NO:4.

16. A pharmaceutical composition comprising the protein of claim 15 and pharmaceutically acceptable carrier or auxiliary substances, diluents of fillers.

17. The heterodimeric protein of claim 15, wherein the other member of the TGF-β family is activin/inhibitin or a bone morphogenetic protein.

18. A homodimeric protein comprising two monomers of a protein that has an amino acid sequence selected from group consisting of a mature protein that starts with amino acid 236 and ends with amino acid 352 of SEQ ID NO:2, a mature protein that starts with amino acid 237 and ends with amino acid 352 of SEQ ID NO:2, a mature protein that starts with amino acid 236 and ends with amino acid 352 of SEQ ID NO:4 and a mature protein that starts with amino acid 237 and ends with amino acid 352 of SEQ ID NO:4.

19. A pharmaceutical composition comprising the protein of claim 18 and pharmaceutically acceptable carrier or auxiliary substances, diluents or fillers.

20. A pharmaceutical composition comprising a protein and a pharmaceutically acceptable carrier or auxiliary substances, diluents or fillers, said protein selected from the group consisting of SEQ ID NO:2; SEQ ID NO:4; a mature protein that starts with one of amino acid 217–240 and ends with amino acid 352 of SEQ ID NO:2; a mature protein which comprises at least the region of seven cysteine residues, said region comprising amino acid residues 247–352 of SEQ ID NO:2, a mature protein that starts with one of amino acids 217–240 and ends with amino acid 352 of SEQ ID NO:4; and a mature protein which comprises at least the region of seven cysteine residues, said region comprising amino acid residues 247–352 of SEQ ID NO:4.

* * * * *